(12) United States Patent
Wagner et al.

(10) Patent No.: US 8,298,780 B2
(45) Date of Patent: Oct. 30, 2012

(54) METHODS OF DETECTION OF CHANGES IN CELLS

(75) Inventors: Rick Wagner, Cambridge, MA (US); Rafael Fernandez, Jamaica Plain, MA (US); Brian T. Cunningham, Champaign, IL (US); Lance Laing, Belmont, MA (US)

(73) Assignee: X-Body, Inc., Waltham, MA (US)

( * ) Notice: Subject to any disclaimer, the term of this patent is extended or adjusted under 35 U.S.C. 154(b) by 514 days.

(21) Appl. No.: 12/335,393

(22) Filed: Dec. 15, 2008

(65) Prior Publication Data

US 2009/0130703 A1 May 21, 2009

Related U.S. Application Data

(63) Continuation-in-part of application No. 11/828,076, filed on Jul. 25, 2007, which is a continuation-in-part of application No. 10/667,696, filed on Sep. 22, 2003, now Pat. No. 7,264,973.

(60) Provisional application No. 61/043,478, filed on Apr. 9, 2008.

(51) Int. Cl.
*G01N 33/551* (2006.01)

(52) U.S. Cl. ........... 435/7.2; 385/12; 385/129; 385/130; 422/82.11; 435/288.7; 435/808; 436/164; 436/524; 436/525; 436/805

(58) Field of Classification Search ........................ None
See application file for complete search history.

(56) References Cited

U.S. PATENT DOCUMENTS

| | | | |
|---|---|---|---|
| 3,689,346 A | 9/1972 | Rowland |
| 3,810,688 A | 5/1974 | Ballman et al. |
| 3,856,404 A | 12/1974 | Hershler et al. |
| 4,009,933 A | 3/1977 | Firester |
| 4,050,895 A | 9/1977 | Hardy et al. |
| 4,240,751 A | 12/1980 | Linnecke et al. |
| 4,289,371 A | 9/1981 | Kramer |
| 4,344,438 A | 8/1982 | Schultz |
| 4,420,502 A | 12/1983 | Conley |
| 4,536,608 A | 8/1985 | Sheng et al. |
| 4,560,248 A | 12/1985 | Cramp et al. |
| 4,576,850 A | 3/1986 | Martens |
| 4,608,344 A | 8/1986 | Carter et al. |
| 4,650,329 A | 3/1987 | Barrett et al. |
| 4,652,290 A | 3/1987 | Cho et al. |
| 4,668,558 A | 5/1987 | Barber |
| 4,701,008 A | 10/1987 | Richard et al. |
| 4,810,658 A | 3/1989 | Shanks et al. |
| 4,815,843 A | 3/1989 | Tiefenthaler et al. |

(Continued)

FOREIGN PATENT DOCUMENTS

CA 2394966 8/2001

(Continued)

OTHER PUBLICATIONS

Palmer, "Diffraction Gratings, The Crucial Dispersive Component", Spectroscopy, 10(2), pp. 14-15 (1995).

(Continued)

*Primary Examiner* — Chris L Chin
(74) *Attorney, Agent, or Firm* — McDonnell Boehnen Hulbert & Berghoff LLP

(57) ABSTRACT

Methods are provided to detect changes in cells without the use of detection labels.

9 Claims, 2 Drawing Sheets

U.S. PATENT DOCUMENTS

| | | |
|---|---|---|
| 4,818,710 A | 4/1989 | Sutherland et al. |
| 4,857,273 A | 8/1989 | Stewart et al. |
| RE33,064 E | 9/1989 | Carter |
| 4,876,208 A | 10/1989 | Gustafson et al. |
| 4,882,288 A | 11/1989 | North et al. |
| 4,888,260 A | 12/1989 | Cowan |
| 4,931,384 A | 6/1990 | Layton et al. |
| 4,952,056 A | 8/1990 | Tiefenthaler |
| 4,958,895 A | 9/1990 | Wells et al. |
| 4,992,385 A | 2/1991 | Godfrey |
| 4,999,234 A | 3/1991 | Cowan |
| 5,071,248 A | 12/1991 | Tiefenthaler et al. |
| 5,118,608 A | 6/1992 | Layton et al. |
| 5,155,785 A | 10/1992 | Holland et al. |
| 5,156,785 A | 10/1992 | Zdrahala |
| 5,170,448 A | 12/1992 | Ackley et al. |
| 5,175,030 A | 12/1992 | Lu et al. |
| 5,210,404 A | 5/1993 | Cush et al. |
| 5,216,680 A | 6/1993 | Magnusson et al. |
| 5,229,614 A | 7/1993 | Anderson et al. |
| 5,242,828 A | 9/1993 | Bergström et al. |
| 5,268,782 A | 12/1993 | Wenz et al. |
| 5,310,686 A | 5/1994 | Sawyers et al. |
| 5,337,183 A | 8/1994 | Rosenblatt |
| 5,413,884 A | 5/1995 | Koch et al. |
| 5,442,169 A | 8/1995 | Kunz |
| 5,455,178 A | 10/1995 | Fattinger |
| 5,475,780 A | 12/1995 | Mizrahi |
| 5,478,527 A | 12/1995 | Gustafson et al. |
| 5,478,756 A | 12/1995 | Gizeli et al. |
| 5,492,840 A | 2/1996 | Malmqvist et al. |
| 5,496,701 A | 3/1996 | Pollard-Knight |
| 5,559,338 A | 9/1996 | Elliot et al. |
| 5,598,267 A | 1/1997 | Sambles et al. |
| 5,598,300 A | 1/1997 | Magnusson et al. |
| 5,606,170 A | 2/1997 | Saaski et al. |
| 5,615,052 A | 3/1997 | Doggett |
| 5,629,214 A | 5/1997 | Crosby |
| 5,631,171 A | 5/1997 | Sandstrom et al. |
| 5,666,197 A | 9/1997 | Guerra |
| 5,690,894 A | 11/1997 | Pinkel et al. |
| 5,691,846 A | 11/1997 | Benson et al. |
| 5,732,173 A | 3/1998 | Bylander et al. |
| 5,738,825 A | 4/1998 | Rudigier et al. |
| 5,768,461 A | 6/1998 | Svetkoff et al. |
| 5,771,328 A | 6/1998 | Wortman et al. |
| 5,792,411 A | 8/1998 | Morris et al. |
| 5,801,390 A | 9/1998 | Shiraishi |
| 5,804,453 A | 9/1998 | Chen |
| 5,814,516 A | 9/1998 | Vo-Dinh |
| 5,814,524 A | 9/1998 | Walt et al. |
| 5,821,343 A | 10/1998 | Keogh |
| 5,846,843 A | 12/1998 | Simon |
| 5,864,641 A | 1/1999 | Murphy et al. |
| 5,922,550 A | 7/1999 | Everhart et al. |
| 5,925,878 A | 7/1999 | Challener |
| 5,955,335 A | 9/1999 | Thust et al. |
| 5,955,378 A | 9/1999 | Challener |
| 5,955,729 A | 9/1999 | Nelson |
| 5,986,762 A | 11/1999 | Challener |
| 5,991,480 A | 11/1999 | Kunz et al. |
| 5,994,150 A | 11/1999 | Challener et al. |
| 5,998,298 A | 12/1999 | Hetherington et al. |
| 6,035,089 A | 3/2000 | Grann et al. |
| 6,042,998 A | 3/2000 | Brueck et al. |
| 6,052,213 A | 4/2000 | Burt et al. |
| 6,076,248 A | 6/2000 | Hoopman et al. |
| 6,088,505 A | 7/2000 | Hobbs |
| 6,100,991 A | 8/2000 | Challener |
| 6,128,431 A | 10/2000 | Siminovitch |
| 6,146,593 A | 11/2000 | Pinkel et al. |
| 6,174,677 B1 | 1/2001 | Vo-Dinh |
| 6,185,019 B1 | 2/2001 | Hobbs et al. |
| 6,200,737 B1 | 3/2001 | Walt et al. |
| 6,215,928 B1 | 4/2001 | Friesem et al. |
| 6,218,194 B1 | 4/2001 | Lyndin et al. |
| 6,235,488 B1 | 5/2001 | Tom-Moy et al. |
| 6,303,179 B1 | 10/2001 | Koulik et al. |
| 6,316,153 B1 | 11/2001 | Goodman et al. |
| 6,320,991 B1 | 11/2001 | Challener et al. |
| RE37,473 E | 12/2001 | Challener |
| 6,332,663 B1 | 12/2001 | Puzio et al. |
| 6,338,968 B1 | 1/2002 | Hefti |
| 6,340,598 B1 | 1/2002 | Herron et al. |
| 6,346,376 B1 | 2/2002 | Sigrist et al. |
| 6,377,721 B1 | 4/2002 | Walt et al. |
| 6,395,558 B1 | 5/2002 | Duveneck et al. |
| 6,404,554 B1 | 6/2002 | Lee et al. |
| 6,449,097 B1 | 9/2002 | Zhu et al. |
| 6,558,957 B1 | 5/2003 | Roinestad et al. |
| 6,570,657 B1 | 5/2003 | Hoppe et al. |
| 6,579,673 B2 | 6/2003 | McGrath et al. |
| 6,587,276 B2 | 7/2003 | Daniell |
| 6,661,952 B2 | 12/2003 | Simpson et al. |
| 6,707,561 B1 | 3/2004 | Budach et al. |
| 6,748,138 B2 | 6/2004 | Wang et al. |
| 6,771,376 B2 | 8/2004 | Budach et al. |
| 6,867,869 B2 | 3/2005 | Budach et al. |
| 6,870,624 B2 | 3/2005 | Hobbs et al. |
| 6,870,630 B2 | 3/2005 | Budach et al. |
| 6,902,703 B2 | 6/2005 | Marquiss et al. |
| 6,951,715 B2 * | 10/2005 | Cunningham et al. ............ 435/4 |
| 6,990,259 B2 | 1/2006 | Cunningham |
| 7,023,544 B2 | 4/2006 | Cunningham |
| 7,064,844 B2 | 6/2006 | Budach et al. |
| 7,070,987 B2 | 7/2006 | Cunningham |
| 7,074,311 B1 | 7/2006 | Cunningham |
| 7,094,595 B2 | 8/2006 | Cunningham |
| 7,101,660 B2 | 9/2006 | Cunningham et al. |
| 7,118,710 B2 | 10/2006 | Cunningham |
| 7,142,296 B2 | 11/2006 | Cunningham et al. |
| 7,148,964 B2 | 12/2006 | Cunningham et al. |
| 7,153,702 B2 | 12/2006 | Lin |
| 7,158,230 B2 | 1/2007 | Cunningham |
| 7,162,125 B1 | 1/2007 | Schulz |
| 7,170,599 B2 | 1/2007 | Cunningham et al. |
| 7,175,980 B2 | 2/2007 | Qiu et al. |
| 7,197,198 B2 | 3/2007 | Schulz |
| 7,202,076 B2 | 4/2007 | Cunningham et al. |
| 7,217,574 B2 | 5/2007 | Pien et al. |
| 7,264,973 B2 | 9/2007 | Lin et al. |
| 7,267,993 B2 | 9/2007 | Pentrenko |
| 7,292,336 B2 | 11/2007 | Cunningham et al. |
| 7,298,477 B1 | 11/2007 | Cunningham et al. |
| 7,300,803 B2 | 11/2007 | Lin et al. |
| 7,301,628 B2 | 11/2007 | Cunningham et al. |
| 7,306,827 B2 | 12/2007 | Li et al. |
| 7,309,614 B1 | 12/2007 | Baird |
| 7,312,090 B2 | 12/2007 | Lin et al. |
| 7,327,454 B2 | 2/2008 | Cunningham et al. |
| 7,396,675 B2 | 7/2008 | Pawlak et al. |
| 7,479,404 B2 | 1/2009 | Cunningham |
| 7,483,127 B1 | 1/2009 | Li |
| 7,497,992 B2 | 3/2009 | Cunningham |
| 7,521,769 B2 | 4/2009 | Cunningham |
| 7,524,625 B2 | 4/2009 | Madison |
| 7,534,578 B1 | 5/2009 | Baird |
| 7,620,276 B2 | 11/2009 | Schulz |
| 7,628,085 B2 | 12/2009 | Laing |
| 7,742,662 B2 | 6/2010 | Cunningham |
| 7,756,365 B2 | 7/2010 | Cunningham |
| 7,790,406 B2 | 9/2010 | Cunningham |
| 2002/0018610 A1 | 2/2002 | Challener et al. |
| 2002/0028045 A1 | 3/2002 | Yoshimura |
| 2002/0028480 A1 | 3/2002 | Maher |
| 2002/0123050 A1 | 9/2002 | Poponin |
| 2002/0127565 A1 | 9/2002 | Cunningham et al. |
| 2002/0135752 A1 | 9/2002 | Sokolov et al. |
| 2002/0168295 A1 | 11/2002 | Cunningham et al. |
| 2002/0171045 A1 | 11/2002 | Perraut |
| 2003/0003599 A1 | 1/2003 | Wagner et al. |
| 2003/0017580 A1 | 1/2003 | Cunningham et al. |
| 2003/0017581 A1 | 1/2003 | Li et al. |
| 2003/0026891 A1 | 2/2003 | Qiu et al. |
| 2003/0027327 A1 | 2/2003 | Cunningham et al. |
| 2003/0027328 A1 | 2/2003 | Cunningham et al. |
| 2003/0032039 A1 | 2/2003 | Cunningham et al. |

| | | | |
|---|---|---|---|
| 2003/0059855 A1 | 3/2003 | Cunningham et al. | |
| 2003/0068657 A1 | 4/2003 | Lin et al. | |
| 2003/0077660 A1 | 4/2003 | Pien et al. | |
| 2003/0092075 A1 | 5/2003 | Pepper | |
| 2003/0104479 A1 | 6/2003 | Bright | |
| 2003/0113766 A1 | 6/2003 | Pepper et al. | |
| 2003/0148142 A1 | 8/2003 | Pawlak | |
| 2003/0210396 A1 | 11/2003 | Hobbs et al. | |
| 2003/0224369 A1 | 12/2003 | Surber et al. | |
| 2004/0005540 A1 | 1/2004 | Pentrenko | |
| 2004/0011965 A1 | 1/2004 | Hodgkinson | |
| 2004/0091397 A1 | 5/2004 | Picard | |
| 2004/0132172 A1 | 7/2004 | Cunningham et al. | |
| 2004/0132214 A1 | 7/2004 | Lin et al. | |
| 2004/0132244 A1 | 7/2004 | Lin et al. | |
| 2004/0151626 A1 | 8/2004 | Cunningham et al. | |
| 2004/0191757 A1 | 9/2004 | Maher | |
| 2004/0219619 A1 | 11/2004 | Fernandez-Salas | |
| 2005/0214803 A1 | 9/2005 | Wang | |
| 2005/0227374 A1 | 10/2005 | Cunningham | |
| 2006/0003372 A1 | 1/2006 | Li | |
| 2006/0030033 A1 | 2/2006 | Cunningham | |
| 2006/0040376 A1 | 2/2006 | Cunningham et al. | |
| 2006/0057707 A1 | 3/2006 | Lin et al. | |
| 2006/0181705 A1 | 8/2006 | Cunningham et al. | |
| 2006/0193550 A1 | 8/2006 | Wawro et al. | |
| 2006/0275825 A1 | 12/2006 | Laing et al. | |
| 2006/0281077 A1 | 12/2006 | Lin | |
| 2006/0286663 A1 | 12/2006 | Cunningham et al. | |
| 2007/0015210 A1 | 1/2007 | Ezekiel | |
| 2007/0041012 A1 | 2/2007 | Cunningham et al. | |
| 2007/0054339 A1 | 3/2007 | Lin | |
| 2007/0070355 A1 | 3/2007 | Cunningham et al. | |
| 2007/0141231 A1 | 6/2007 | Cunningham et al. | |
| 2008/0213910 A1 | 9/2008 | Jogikalmath | |
| 2008/0219892 A1 | 9/2008 | Cunningham | |
| 2008/0240543 A1 | 10/2008 | Budach | |
| 2008/0299673 A1 | 12/2008 | Laing et al. | |
| 2009/0017488 A1 | 1/2009 | Binder | |
| 2009/0061416 A1* | 3/2009 | Fang et al. | 435/5 |
| 2009/0093011 A1* | 4/2009 | Fang et al. | 435/29 |
| 2009/0137422 A1 | 5/2009 | Laing | |
| 2009/0148955 A1 | 6/2009 | Cunningham | |
| 2009/0176658 A1 | 7/2009 | Madison | |
| 2009/0179637 A1 | 7/2009 | Cunningham | |
| 2009/0192049 A1 | 7/2009 | Laing | |
| 2009/0227469 A1 | 9/2009 | Conklin | |
| 2009/0264314 A1 | 10/2009 | Cunningham | |
| 2009/0269244 A1 | 10/2009 | Cunningham | |
| 2009/0282931 A1 | 11/2009 | Laing | |
| 2009/0305304 A1 | 12/2009 | Laing | |
| 2010/0003743 A1 | 1/2010 | Schulz | |
| 2010/0008826 A1 | 1/2010 | Schulz | |
| 2010/0015721 A1 | 1/2010 | Laing | |
| 2010/0043571 A1 | 2/2010 | Laing | |
| 2010/0143959 A1 | 6/2010 | Cunningham | |
| 2010/0195099 A1 | 8/2010 | Rockney | |
| 2010/0196925 A1 | 8/2010 | Genick | |
| 2010/0202923 A1 | 8/2010 | Cunningham | |
| 2010/0227769 A1 | 9/2010 | Schulz | |
| 2010/0231907 A1 | 9/2010 | Pien | |
| 2010/0291575 A1 | 11/2010 | Shamah | |

FOREIGN PATENT DOCUMENTS

| | | | |
|---|---|---|---|
| CA | 2395318 | | 8/2001 |
| CH | 6 690 50 A5 | | 2/1989 |
| CH | 6 705 21 A5 | | 6/1989 |
| EP | 0 075 353 | | 3/1983 |
| EP | 0 112 721 | | 7/1984 |
| EP | 0 326 219 | | 1/1989 |
| EP | 0 517 777 | | 5/1996 |
| EP | 0 660 924 | | 9/1999 |
| EP | 1031828 | | 8/2000 |
| EP | 1085315 | | 3/2001 |
| FR | 2 801 977 | | 12/1999 |
| GB | 2 156 970 A | | 10/1985 |
| GB | 2 227 089 | | 7/1990 |
| JP | 1993-228946 | | 9/1993 |
| WO | WO 81/00912 | | 2/1981 |
| WO | WO 84/02578 | | 7/1984 |
| WO | WO 86/07149 | | 12/1986 |
| WO | WO 90/08313 | | 7/1990 |
| WO | WO 91/13339 | | 9/1991 |
| WO | WO 92/04653 | | 3/1992 |
| WO | WO 92/21768 | | 12/1992 |
| WO | WO 93/14392 | | 7/1993 |
| WO | WO 95/03538 | | 2/1995 |
| WO | WO 96/38726 | | 12/1996 |
| WO | WO 97/29362 | | 8/1997 |
| WO | WO 98/10288 | | 3/1998 |
| WO | WO 98/57200 | | 12/1998 |
| WO | WO 99/09392 | | 2/1999 |
| WO | WO 99/09396 | | 2/1999 |
| WO | WO 99/54714 | | 10/1999 |
| WO | WO 99/66330 | | 12/1999 |
| WO | WO 00/23793 | | 4/2000 |
| WO | WO 00/29830 | | 5/2000 |
| WO | WO 01/02839 | | 1/2001 |
| WO | WO 01/04697 | | 1/2001 |
| WO | WO 01/79559 | | 10/2001 |
| WO | WO 01/92870 | | 12/2001 |
| WO | WO 02/061429 | | 8/2002 |
| WO | 03/074548 | | 9/2003 |
| WO | WO 2006108183 | * | 10/2006 |
| WO | 2007/064702 | | 6/2007 |
| WO | 2008106048 | | 9/2008 |
| WO | 2009/009718 | | 1/2009 |
| WO | 2010005600 | | 1/2010 |
| WO | 2010/075033 | | 7/2010 |

OTHER PUBLICATIONS

Bandell et al., "Noxious Cold Ion Channel TRPA1 is Activated by Pungent Compounds and Bradykinin" Neuron, vol. 41, pp. 849-957 (2004).

Cunningham et al., "Label-Free Assays on the BIND System", Journal of Biomolecular Screening, 9:481 (2004).

IMT Applied Optics, "Resonant Grating Filters", 2008.

Cunningham et al., "Advantages and application of label-free detection assays in drug screening", Expert Opin. Drug Discovery, 3:891-901 (2008).

U.S. Appl. No. 60/244,312, filed Oct. 30, 2000, Cunningham, et al.

U.S. Appl. No. 60/283,314, filed Apr. 12, 2001, Cunningham, et al.

U.S. Appl. No. 60/303,028, filed Jul. 3, 2001, Cunningham, et al.

Brecht, et al., "Optical probes and transducers", *Biosensors & Bioelectronics* vol. 10, pp. 923-936 (1995).

Challener, et al., "A multilayer grating-based evanescent wave sensing technique", *Sensors and Actuators B*, 71, pp. 42-46 (2000).

Cowan, "Aztec surface-relief volume diffractive structure", *J. Opt. Soc. Am.*, vol. 7, No. 8, pp. 1529-1544 (1990).

Cowan, "Holographic honeycomb microlens", *Optical Engineering*, vol. 24, No. 5, pp. 796-802 (1985).

Cowan, "The Recording and Large Scale Replication of Crossed Holographic Grating Arrays using Multiple Beam Interferometry", *SPIE* vol. 503, Application, Theory, and Fabrication of Periodic Structures, pp. 120-129 (1984).

Cowan, et al., "The Recording and Replication of Holographic Micropatterns for the Ordering of Photographic Emulsion Grains in Film Systems", *J. Imaging Sci.*, vol. 31, No. 3, pp. 100-107 (1987).

Cunningham, "Optically Based Energy Transduction", *Techniques in Analytical Chemistry*, pp. 260-291 (1998).

Hobbs, et al., "Automated Interference Lithography Systems for Generation of Sub-Micron Feature Size Patterns", *SPIE*, vol. 3879, pp. 124-135, (1999).

Huber, et al., "Direct optical immunosensing sensitivity and selectivity)", *Sensors and Actuators B*, 6, pp. 122-126 (1992).

Jenison, et al., "Interference-based detection of nucleic acid targets on optically coated silicon", *Nature Biotechnology*, vol. 19, pp. 62-64 (2001).

Jin, et al., "A biosensor concept based on imaging ellipsometry for visualization of biomolecular interactions", *Analytical Biochemistry*, vol. 232, pp. 69-72 (1995).

Jordan, et al., "Surface Plasmon Resonance Imaging Measurements of Electrostatic Biopolymer Adsorption onto Chemically Modified Gold Surfaces", *Analytical Chemistry*, vol. 69, No. 7, pp. 1449-1456 (1997).

Lin, et al., "A Porous Silicon-Based Optical Interferomettic Biosensor", *Science*, vol. 278, pp. 840-843 (1997).
Magnusson, et al., "New principle for optical filters", *Appl. Phys. Lett.*, vol. 61, No. 9, pp. 1022-1024 (1992).
Magnusson, et al., "Transmission bandpass guided-mode resonance filters", *Applied Optics*, vol. 34, No. 35, pp. 8106-8109 (1995).
Morhard, et al., "Immobilization of antibodies in micropatterns for cell detection by optical diffraction", *Sensors and Actuators* B 70, pp. 232-242 (2000).
Pandey, et al., "Proteomics to study genes and genomes", *Nature* 405(6788):837-46 (2000).
Patel, et al., "Electrically tuned and polarization insensitive Fabry-Perot etalon with a liquid-crystal film", *Appl. Phys. Lett.*, vol. 58, No. 22, pp. 2491-2493 (1991).
Bertoni, et al., "Frequency-Selective Reflection and Transmission by a Periodic Dielectric Layer", *IEEE Transactions on Antennas and Propagation*, vol. 37, No. 1, pp. 78-83 (1989).
Brundrett, et al., "Normal-incidence guided-mode resonant grating filters: design and experimental demonstration", *Optics Letters*, vol. 23, No. 9, pp. 700-702 (1998).
Peng, "*Polarization-control Components and Narrow-band Filters Based on Subwavelength Grating Structures*" 1996.
Statement of Applicants dated May 10, 2004.
Leanu, Torben, *Material, Silicon Nitride*, 1996, 97, 98.
Cerac, Technical publications: *Tantalum Oxide, $Ta_2O_5$ for Optical Coating*, 2000, Cerac, Inc.
Neuschafer et al., Evanescent resonator chips: a universal platform with superior sensitivity for fluorescence-based microarrays. Biosensors & Bioelectronics, 18 (2003) 489-497.
Budach et al., Generation of transducers for fluorescence-based microarrays with enhanced sensitivity and their application for gene expression profiling. Analytical Chemistry. Jun. 1, 2003;75(11):2571-7.
Anderson, et al., "Proteomics: applications in basic and applied biology", *Current Opinion in Biotechnology*, 2000, 11:408-412.
MacBeath, et al., "Printing Proteins as Microarrays for High-Throughput Function Determination", *Science*, vol. 289, pp. 1760-1763, 2000.
deWildt, et al., "Antibody arrays for high-throughput screening of antibody-antigen interactions", *Nature Biotechnology*, vol. 18, pp. 989-994, 2000.
Cunningham, et al., "A plastic colorimetric resonant optical biosensor for multiparallel detection of label-free biochemical interactions", *Sensors and Actuators B*, 85 (2002) 219-226.
Caruso, et al., "Quartz Crystal Microbalance Study of DNA Immobilization and Hybridization for Nucleic Acid Sensor Development", *Analytical Chemistry*, vol. 69, No. 11, pp. 2043-2049, 1997.
Hefti, et al, "Sensitive detection method of dielectric dispersions in aqueous-based, surface-bound macromolecular structures using microwave spectroscopy", *Applied Physics Letters*, vol. 75, No. 12, pp. 1802-1804, 1999.
Wu, et al., "Bioassay of prostate-specific antigen (PSA) using microcantilevers", *Nature Biotechnology*, vol. 19, pp. 856-860, 2001.
Wasserman, et al., "Structure and Reactivity of Alkylsiloxane Monolayers Formed by Reaction of Alkyltrichlorosilanes on Silicon Substrates", *Langmuir*, 5, 1074-1087, 1989.
Kallury, et al., "X-ray Photoelectron Spectroscopy of Silica Surfaces Treated with Polyfunctional Silanes", *Anal. Chem.*, 60, 169-172, 1988.
Cunningham, et al., "Colorimetric resonant reflection as a direct biochemical assay technique", *Sensors and Actuators B*, 81 (2002) 316-328.
Mullaney, et al., "Epitope Mapping of Neutralizing Botulinum Neurotoxin A Antibodies by Phage Display", *Infection and Immunity*, vol. 69, No. 10, pp. 6511-6514, 2001.
Nellen, et al., "Integrated Optical Input Grating Couplers as Biochemical Sensors", *Sensors and Actuators*, 15 (1988) 285-295.
Lukosz and Tiefenthaler, "Embossing technique for fabricating integrated optical components in hard inorganic waveguiding materials," *Optics Letters*, vol. 8, pp. 537-539 (1983).
Tiefenthaler and Lukosz, "Integrated optical switches and gas sensors," *Optics Letters*, vol. 10, pp. 137-139 (1984).
Chabay, "Optical Waveguides," *Analytical Chemistry*, vol. 54, pp. 1071A-1080A (1982).
Sutherland et al., "Optical Detection of Antibody-Antigen Reactions at a Glass-Liquid Interface," *Clin. Chem.*, vol. 30, pp. 1533-1538 (1984).
Holm and Palik, "Internal-reflection spectroscopy," *Laser Focus*, vol. 15, pp. 60-65 (Aug. 1979).
Harrick and Loeb, "Multiple Internal Reflection Fluorescence Spectrometry," *Analytical Chemistry*, vol. 45, pp. 687-691 (1973).
Tien, "Light Waves in Thin Films and Integrated Optics," *Applied Optics*, vol. 10, pp. 2395-2413 (1971).
Dakss et al., "Grating Coupler for Efficient Excitation of Optical Guided Waves in Thin Films," *Applied Physics Letters*, vol. 16, pp. 523-525 (1970).
Sutherland et al., "Immunoassays at a Quartz-Liquid Interface: Theory, Instrumentation and Preliminary Application to the Fluorescent Immunoassay of Human Immunoglobulin G," *Journal of Immunological Methods*, vol. 74, pp. 253-265 (1984).
English translation of CH 670 521 A5, Jun. 15, 1989.
English translation of CH 669 050 A5, Feb. 15, 1989.
Patel, et al., "Multi-vwavelength Tunable Liquid-Crystal Etalon Filter", *IEEE Photonics Technology Letters*, vol. 3, No. 7, pp. 643-644 (1991).
Patterson, S.D., "Proteomics: the industrialization of protein chemistry", *Current Opinions in Biotechnology*. 11(4):413-8 (2000).
Peng, et el., "Experimental demonstration of resonant anomalies in diffraction from two-dimensional gratings", *Optics Letters* vol. 21, No. 8, pp. 549-551 (1996).
Peng, et al., "Resonant scattering from two-dimensional gratings", *J. Opt. Soc. Am. A.*, vol. 13, No. 5, pp. 993-1005 (1996).
Raguin, et al., "Structured Surfaces Mimic Coating Performance", *Laser Focus World*, pp. 113-117 (1997).
Sigal, et al., "A Self-Assembled Monolayer for the Binding and Study of Histidine-Tagged Proteins by Surface Plasmon Resonance", *Analytical Chemistry*, vol. 68, No. 3, pp. 490-497 (1996).
Wang, et al., "Design of waveguide-grating filters with symmetrical line shapes and low sidebands", *Optical Society of America*, vol. 19, No. 12, 919-921 (1994).
Wang, et al., "Guided-mode resonances in planar dielectric-layer diffraction gratings", *J. Opt. Soc. Am.*, vol. 7, No. 8, pp. 1470-1474 (1990).
Wang, et al., "Theory and applications of guided-mode resonance filter", *Applied Optics*, vol. 32, No. 14, pp. 2606-2613 (1993).
International Search Report for foreign counterpart application PCT/US01/50723, Sep. 17, 2002.
International Search Report for foreign counterpart application PCT/US03/01175, Aug. 18, 2003.
Invitation to Pay Additional Fees in foreign counterpart application PCT/US01/50723, Aug. 30, 2002.
Haidner, "Zero-Order Gratings Used as an Artificial Distributed Index Medium", *Optik, Wissenschaftliche Verlag GmbH*, Stuttgart, DE, vol. 89, No. 3, pp. 107-112, 1992.
Peng, et al., "Experimental Demonstration of Resonant Anomalies in Diffraction from two-Dimensional Gratings", *Optics Letters, Optical Society of America*, vol. 21, No. 9, pp. 549-551, 1996.
Wilson, et al., "The Optical Properties 1-19 of 'Moth Eye' Antireflection Surfaces", *Optica ACTA*, vol. 29, No. 7, pp. 993-1009, 1982.
Bagnich, et al., "*Tunable Optical Filter*", Derwent Publications, English Translation, Abstract Only, Derwent Publications Ltd. (1989).
*Corning, Inc. v. SRU Biosystems, Inc.*, Memorandum Opinion dated Nov. 15, 2005 in the United States District Court for the district of Delaware.
Liu, et al., "*Development of an optical fiber lactate sensor*", Mikrochimica Acta, 1999, 131(1-2), pp. 129-135.
U.S. Appl. No. 11/635,934, filed Dec. 8, 2006.
U.S. Appl. No. 11/566,818, filed Dec. 5, 2006.
U.S. Appl. No. 11/506,639, filed Aug. 18, 2007.
U.S. Appl. No. 11/749,073, filed May 15, 2007.
U.S. Appl. No. 11/828,076, filed Jul. 25, 2007.
European Search Report for EP 07 11 8355 dated Feb. 5, 2008.

Nelson, et al., "BIA/MS of Epitope-Tagged Peptides Directly from *E. coli* Lysate: Multiplex Detection and Protein Identification at Low-Femtomole to Subfemtomole Levels" Anal. Chem. 1999, 71, 2858-2865.
Moffatt, "Optical Probes May Hasten Shift of Diagnostics from Lab to Doc's Office" Genetic Engineering News, vol. 18 (1986) p. 18.
Williams, et al., "The integration of SPR biosensors with mass spectrometry: possible applications for proteome analysis", Trends in Microbiology, Elsevier, vol. 18, No. 2, (2000) pp. 45-48.
Cekaite, et al., "Analysis of the humoral immune response to immunoselected phage-displayed peptides by a microarray-based method", Proteomics 2004, 4, 2572-2582.
Sun, et al., "Use of bioluminescent Salmonella for assessing the efficiency of constructed phage-based biosorbent", Journal of Industrial Microbiology & Biotechnology, 2000, 25, 273-275.
Wan, et al., "Landscape phage-based magnetostrictive biosensor for detecting *Bacillus anthracis* spores", Proc. IEEE Sens., 2005, 1308-1311.
Cunningham, et al. "Label-Free Assays on the BIND System", The Society for Biomolecular Screening, p. 481490 (2004).
Cunningham, "Label-Free Detection with the BIND System", Presented at Screentech General, Mar. 24, 2003.
Baird, "Beyond ELISA's: Label-free Detection with BIND", Presented at Interphex Meeting in Europe, Mar. 16-18, 2004.
Cunningham, et al., "Colorimetric Resonant Reflection as a Direct Biochemical Assay Technique", Presented at the Pittsburgh Conference and Exposition on Anayltical Chemistry and Applied Spectroscopy, Morial Convention Center in New Orleans, LA, Mar. 17-22, 2002.
Broad, et al. "Growth and adipose differentiation of sheep preadipocyte fibroblasts in serum-free medium", Eur. J. Bichem, 135, 33-39 (1983).
Castillo et al., "Characterization of proliferation and differentiation of EGF-responsive striatal and septal precursor cells", Int. J. Devl. Neuroscience 21 (2003) 41-47.
Chalazonitis, et al., "The α1 Subunit of Laminin-1 Promotes the Development of Neurons by Interacting with LBP110 Expressed by Neural Crest-Derived Cells Immunoselected from the Fetal Mouse Gut", J. Neurobiol, 33:118-138 1997.
Hao et al., "Fetal Human Hemotopoietic Stem Cells Can Differentiate Sequentially into Neural Stem Cells and Then Astrocytes in Vitro", Journal of Hematotherapy & Stem Cell Research, 12:23-32 (2003).
Kano, et al., "Establishment of Hepatic Stem-like Cell Lines from Normal Adult Porcine Liver in a Poly-D-Lysine-Coated Dish with Nair-1 Medium", In Vitro Cell. Dev. Biol.—Animal, 30:440-448 (2003).
Sung, et al., "Adhesiveness of Human Ligament Fibroblasts to Laminin", Journal of Orthopaedic Research, 13:166-173 1995.
Zhou, et al., "Long-term nonpassaged EGF-responsive neural precursor cells are stem cells", Wound Repair and Regeneration, vol. 6, No. 4, pp. 337-348 1998.
Adamczyk, et al., "Application of Surface Plasmon Resonance toward Studies of Low-Molecular-Weight Antigen-Antibody Binding Interactions", Methods, 20, pp. 319-328 2000.
Marquart, "Immobilization Techniques", SPR pages [online] Jan. 2004 pp. 1-7.
Zhang, et al., "Use of surface Plasmon resonance for the measurement of low affinity binding interactions between HSP72 and measles virus nucleocapsid protein", Biol. Proced. Online 2003;5(1):170-181.
Gestwicki, et al., "Using Receptor Conformational Change to Detect Low Molecular Weight Analytes by Surface Plasmon Resonance", Anal. Chem., 2001, 4., 5732-5737.
International Search Report dated Jul. 15, 2008 for PCT application serial No. PCT/US08/60951.
English machine translation only of JP 1993-228946 Sep. 7, 1993.
U.S. Appl. No. 12/171,475, filed Jul. 11, 2008.
U.S. Appl. No. 12/335,393, filed Dec. 15, 2008.
International Search Report for corresponding application No. PCT/US09/30412 dated Jan. 8, 2009.
Tai, et al., "Insulin-like Growth Factor-1 Induces Adhesion and Migration in Human Multiple Myeoloma Cells via Activation of B1-Integrin and Phosphatidylinositol 3'-Kinase/AKT Signaling", Cancer Research, 63, 5850-5858 (2003).
Holt, et al., "Human myelcoma cells adhere to fibronectin in response to hepatocyte growth factor", The Hematology Journal, 90(4), 479-488 (2005).
Galownia, et al., "Selective Desensitization of Growth Factor Signaling by Cell Adhesion to Fibronectin", The Journal of Biological Chemistry, vol. 282, No. 30, pp. 21758-21766 (2007).
Manevich, et al., "Talin 1 and Paxillin Facilitate Distinct Steps to Rapid VLA-4-mediated Adhesion Strengthening to Vascular Cell Adhesion Molecule 1", The Journal of Biological Chemistry, vol. 282, No. 35, pp. 25338-25348 (2007).
Edderkaoui, et al., "Insulin-like Growth Factor-I Receptor Mediates the Prosurvival Effect of Fibronectin", The Journal of Biological Chemistry, vol. 282, No. 37, pp. 26646-26655 (2007).
Arcangeli, et al., "Complex functional interaction between integrin receptors and ion channels", Trends in Cell Biology, vol. 16, No. 12, pp. 631-639 (2006).
Bijian, et al., "Collagen-mediated survival signaling is modulated by CD45 in Jurkat T. cells", Mol. Immunol. 44 (15):3682-90 (2007), Abstract only.
Chetoui, et al., "Collagen type I-mediated activation of ERK/MAP Kinase is dependent on Ras, Raf-1 and protein phosphatase 2A in Jurkat T cells", Mol. Immuno., 43(10):1687-93 (2006), Abstract Only.
Juliano, "Signal Transduction by Cell Adhesion Receptors and the Cytoskeleton: Functions of Integrins, Cadherins, Selectins, and Immunoglobulin-Superfamily Members", Annu. Rev. Pharmcol. Toxicol. 42:283-323 (2002).
Cooper, "Current biosensor technologies during drug discovery", Drug Discovery World Summer 2006, pp. 68-82.
Comley, "Label-Free Detection New biosensors facilitate broader range of drug discovery applications", Drug Discovery World Winter May 2004, pp. 63-74.
Cunningham, "Colorimetric Resonant Reflection as a Direct Biochemical Assay Technique", IEEE, Annual International Conference on Micro Electro Mechanical Systems, MEMS, 2002, Las Vegas, NV Jan. 20-24, 2002.
International Search Report and Written Opinion for corresponding application No. PCT/US09/67880 dated Mar. 5, 2010.
Wawro et al., "Optical fiber endface biosensor based on resonances in dielectric waveguide gratings", Biomedical Diagnostic Guidance and Surgical-Assist Systems II, Vo-Dihn et al. eds., Proceedings of SPIE, vol. 3911 (2000), p. 86-94.
Office Action dated Apr. 2, 2007 for U.S. Appl. No. 11/506,639 (now U.S. Patent No. 7,298,477).
Ramsden et al., "Optical Method for Measurement of Number and Shape of Attached Cells in Real Time", Cytometry, vol. 19, pp. 97-102 (1995).
Li et al., "Measurement of Adhesion and Spreading Kinetics of Baby Hamster Kidney and Hybridoma Cells Using an Integrated Optical Method"; Biotechnol. Prog., vol. 10, pp. 520-524 (1994).
Takeda et al., "The Integrins", Genome Biology, 8:215 (2007).
Sancho et al., "Binding kinetics of monomeric and aggregated IgG to Kupffer cells and hepatocytes of mice", Immunology, 53:283 (1984).
Chaplen et al., "Improvement of Bioactive Compound Classification through Integration of Orthogonal Cell-Based Biosensing Methods", Sensors, 7:38-51 (2007).
U.S. Appl. No. 13/166,936, filed Jun. 23, 2011.
U.S. Appl. No. 13/073,233, filed Mar. 28, 2011.
Lin et al., "A label-free biosensor-based cell attachment assay for characterization of cell surface molecules", Sensors and Actuators B, vol. 114, p. 559-564 (2006).
Hug et al. "Optical waveguide lightmode spectroscopy as a new method to study adhesion of anchorage-dependent cells as an indicator of metabolic state", Biosensors & Bioelectronics, 16:865-874 (2001).
Fang et al., "Dynamic mass redistribution: a novel physiological signal of cells for cell systems biology and pharmacology", catalogcorning.com, p. 1-4 (2007).
Fang, "Non-Invasive Optical Biosensor for Probing Cell Signaling", Sensors, 7:2316-2329 (2007).
Barnes et al., "Induction of RANTES expression by astrocytes and astrocytoma cell lines", Journal of Neuroimmunology, 71:207-214 (1996).

\* cited by examiner

METHODS OF DETECTION OF CHANGES IN CELLS

PRIORITY

This application claims the benefit of U.S. application Ser. No. 61/043,478, filed Apr. 9, 2008 and is a continuation in part of U.S. Ser. No. 11/828,076, filed Jul. 25, 2007, which is a continuation in part of U.S. Ser. No. 10/667,696, filed Sep. 22, 2003, now U.S. Pat. No. 7,264,973, which are incorporated herein by reference in their entirety.

This application cross-references U.S. Ser. No. 12/335,433, entitled "Methods For Identifying Modulators of Ion Channels," filed Dec. 15, 2008, which is incorporated by reference herein in its entirety.

BACKGROUND OF THE INVENTION

The science of drug discovery is in need of more efficient tools for the determination of the effect of biological materials and test compounds upon human cells and tissues. Often many biological platforms, some using engineered cells or labels, are established within an organization for these determinations in cell based systems. These platforms require many different readouts that often provide inconsistent data sets. They often employ the use of engineered cells containing the overexpression of a particular target involved in a disease process. The net effect of such an engineered system is exactly the opposite of what was initially sought; the outcome is removed from the natural or native response. In other cases, platforms employ the use of labels to monitor the outcome of an experiment. The introduction of new chemical entities in the labels also can have significant effect on the outcome of the experiment in ways difficult to determine. What is desired is a single platform that could be used with many different types of cells for the testing of potential therapeutics that reflect the native cell reaction to the test materials.

SUMMARY OF THE INVENTION

One embodiment of the invention provides a method of detection of responses of cells to stimuli. The method comprises:
(i) immobilizing one or more extracellular matrix ligands to a surface of a colorimetric resonant reflectance biosensor or a grating-based waveguide biosensor, wherein the cells have cell surface receptors specific for the one or more extracellular matrix ligands; and adding the cells to the biosensor; or
(ii) mixing cells with one or more extracellular matrix ligands, wherein the cells have cell surface receptors specific for the one or more extracellular matrix ligands; and adding the cells with one or more extracellular matrix ligands to a surface of a colorimetric resonant reflectance biosensor or a grating-based waveguide biosensor. The cells in both instances can be in serum-free medium. The cells are exposed to stimuli and the response of the cells to stimuli is detected. The stimuli can be a compound that modulates activity of a G protein-coupled receptor, an ion channel, P13 kinase, transient receptor potential channels, phospholipase C, receptor tyrosine kinases, cytokines, beta-arrestin pathway responses, cytoskeletal rearrangements, epigenetic signals, or signal transduction pathways. The detection of responses of cells to stimuli can be augmented as compared to methods where one or more extracellular matrix ligands are not included in the detection methodology.

Another embodiment of the invention provides a method of preparing cells for an assay. The method comprises: washing cells with a buffered saline solution lacking calcium and magnesium; removing the buffered saline solution lacking calcium and magnesium from the cells; adding an isotonic ethylenediaminetetraacetate chealating agent to the cells; neutralizing the isotonic ethylenediaminetetraacetate chealating agent with buffered saline solution; washing the cells with buffered saline solution; and adding the cells to a biosensor surface and allowing the cells to attach to the surface of the biosensor. The cells can be added to the biosensor surface in the presence of an adhesion modulator. The biosensor surface can have one or more extracellular matrix ligands immobilized to it or wherein the cells are mixed with one or more extracellular ligands before they are added to the biosensor surface. The binding of the cells to the extracellular matrix ligands can be detected.

Even another embodiment of the invention provides a method of detection of responses of cells to stimuli. The method comprises washing the cells with buffered saline solution. Then:
(i) immobilizing one or more extracellular matrix ligands to a surface of a colorimetric resonant reflectance biosensor or a grating-based waveguide biosensor, wherein the cells have cell surface receptors specific for the one or more extracellular matrix ligands; and adding the cells to the biosensor; or
(ii) mixing cells with one or more extracellular matrix ligands, wherein the cells have cell surface receptors specific for the one or more extracellular matrix ligands; and adding the cells with one or more extracellular matrix ligands to a surface of a colorimetric resonant reflectance biosensor or a grating-based waveguide biosensor.
The cells are exposed to stimuli and the response of the cells to the stimuli is detected. Prior to the listed steps of the method, the following steps can be performed: washing cells with a buffered saline solution lacking calcium and magnesium; removing the buffered saline solution lacking calcium and magnesium from the cells; adding an isotonic ethylenediaminetetraacetate chealating agent to the cells; and neutralizing the isotonic ethylenediaminetetraacetate chealating agent with buffered saline solution. The cells can be added to the biosensor surface in the presence of an adhesion modulator. The stimuli can be a compound that modulates activity of a G protein-coupled receptor, an ion channel, P13 kinase, transient receptor potential channels, phospholipase C, receptor tyrosine kinases, cytokines, beta-arrestin pathway responses, cytoskeletal rearrangements, epigenetic signals, or signal transduction pathways.

Still another embodiment of the invention provides a method of determining if a test reagent affects movement of cells. The method comprises immobilizing one or more extracellular matrix protein ligands to the bottom of a well of a microtiter plate, wherein the bottom of the well comprises a colorimetric resonant reflectance biosensor or a grating-based waveguide biosensor, and wherein the well has a microfluidic channel that can deliver a test reagent to one location within the well. Cells that have cell surface receptors specific for the one or more extracellular matrix protein ligands are added to the well. A test reagent is added to the well using the microfluidic channel; wherein the test reagent is a suspected chemotactic agent. Movement of the cells in the well is detected, wherein if movement of the cells in the well is detected, then the test reagent affects movement of the cells. The test reagent can be a compound that modulates activity of a G protein-coupled receptor, an ion channel, P13 kinase, transient receptor potential channels, phospholipase C, receptor tyrosine kinases, cytokines, beta-arrestin pathway responses, cytoskeletal rearrangements, epigenetic signals, or signal transduction pathways.

Yet another embodiment of the invention provides a method of determining if a test compound affects specific binding of cells to extracellular matrix ligands. The method comprises adding first cells to a first colorimetric resonant reflectance biosensor surface or a first grating-based waveguide biosensor surface, wherein the biosensor surface comprises immobilized extracellular matrix ligands, wherein the first cells have cell surface receptors specific for the extracellular matrix ligands, allowing the first cells to attach to the surface of the first biosensor, and determining a peak wavelength value or signal for the first cells. Second cells are added to a second colorimetric resonant reflectance biosensor surface or a second grating-based waveguide biosensor surface, wherein the second biosensor surface comprises immobilized extracellular matrix ligands, wherein the second cells have cell surface receptors specific for the extracellular matrix ligands, adding a test compound to the biosensor surface, allowing the second cells to attach to the surface of the biosensor, and determining a peak wavelength value or signal for the second cells. The peak wavelength value or signal obtained for the first cells is compared to the peak wavelength value or signal for the second cells; wherein if the peak wavelength value or signal for the second cells is substantially different from the peak wavelength value or signal for the first cells, then the test compound affects specific binding of cells to extracellular matrix ligands. The test compound can be a compound that modulates activity of a G protein-coupled receptor, an ion channel, P13 kinase, transient receptor potential channels, phospholipase C, receptor tyrosine kinases, cytokines, beta-arrestin pathway responses, cytoskeletal rearrangements, epigenetic signals, or signal transduction pathways.

Another embodiment of the invention provides a method of analyzing cell changes in real time. The method comprises immobilizing one or more extracellular matrix ligands to the surface of a colorimetric resonant reflectance biosensor or a grating-based waveguide biosensor; adding cells to the biosensor, wherein the cells have cell surface receptors specific for the one or more extracellular matrix ligands; exposing the cells to stimuli; and detecting the response of the cells to the stimuli using a detection device with a resolution of about 2 to 10 micrometers. The stimuli can be a compound that modulates activity of a G protein-coupled receptor, an ion channel, P13 kinase, transient receptor potential channels, phospholipase C, receptor tyrosine kinases, cytokines, beta-arrestin pathway responses, cytoskeletal rearrangements, epigenetic signals, or signal transduction pathways. The cell changes can be changes in cell growth patterns, cell death patterns, cell movement, cell size or volume, or cell adhesion.

Still another embodiment of the invention provides a method of detecting changes in cell responses. The method comprises immobilizing one or more extracellular matrix ligands to the surface of a colorimetric resonant reflectance biosensor or a grating-based waveguide biosensor; adding cells to the biosensor in serum-free medium, wherein the cells have cell surface receptors specific for the one or more extracellular matrix ligands; exposing the cells to stimuli without washing off the serum free-medium; and detecting the response of the cells to the stimuli. The stimuli can be a compound that modulates activity of a G protein-coupled receptor, an ion channel, P13 kinase, phospholipase C, receptor tyrosine kinases, cytokines, beta-arrestin pathway responses, cytoskeletal rearrangements, epigenetic signals, or signal transduction pathways.

Yet another embodiment of the invention provides a colorimetric resonant reflectance biosensor or a grating-based waveguide biosensor surface, wherein the biosensor is prepared by applying two or more types of extracellular matrix ligands, and ovalbumin or fetal bovine serum to a surface of the biosensor and drying the surface of the biosensor.

Even another embodiment of the invention provides a method of identifying a compound that affects adhesion of cells. The method comprises:

(i) immobilizing one or more extracellular matrix ligands to a surface of a colorimetric resonant reflectance biosensor or a grating-based waveguide biosensor, wherein the cells have cell surface receptors specific for the one or more extracellular matrix ligands; and adding the cells to the biosensor; or (ii) mixing cells with one or more extracellular matrix ligands, wherein the cells have cell surface receptors specific for the one or more extracellular matrix ligands; and adding the cells with one or more extracellular matrix ligands to a surface of a colorimetric resonant reflectance biosensor or a grating-based waveguide biosensor.

The cells are treated with a test compound. A colorimetric resonant reflectance optical first PWV or signal is detected and compared to a second PWV or signal from control cells that were not treated with the test compound to determine if the test compound affects adhesion of the cells. The test compound can be a compound that modulates activity of a G protein-coupled receptor, an ion channel, P13 kinase, transient receptor potential channels, or phospholipase C. During the assay, prior to, or during the addition, or after the addition of the test compound, an adhesion modulator can be added to the cells, wherein the control cells are also treated with the adhesion modulator.

Another embodiment of the invention provides a method of identifying a modified extracellular matrix (ECM) ligand that affects adhesion of cells. The method comprises applying cells to a surface of a colorimetric resonant reflectance optical biosensor or a grating-based waveguide biosensor, wherein modified ECM ligands are immobilized to the surface of the biosensor; adding an adhesion modulator to the cells; detecting a colorimetric resonant reflectance optical first PWV or signal for the cells and comparing the first PWV or signal to a second PWV or signal from control cells that were added to a surface of a colorimetric resonant reflectance optical biosensor or the grating-based waveguide biosensor, wherein non-modified ECM ligands are immobilized to the surface of the biosensor to determine if the test compound affects adhesion of the cells.

Still another embodiment of the invention provides a method of determining if a transfected cell produces a recombinant protein. The method comprises immobilizing one or more extracellular matrix ligands to the surface of a colorimetric resonant reflectance biosensor or a grating-based waveguide biosensor; adding cells that have been transfected with a nucleic acid molecule that encodes a recombinant protein and that have cell surface receptors specific for the one or more extracellular matrix ligands to the surface of the biosensor; determining a first PWV or signal for the cells; adding a modulator that causes a differential response in the transfected cells that expresses the recombinant protein as compared to transfected cells that do not express the recombinant protein; determining a second PWV or signal for the cells; comparing the first peak wavelength value or signal to the second peak wavelength value or signal; wherein if the second peak wavelength value or signal is substantially different from the first peak wavelength value or signal, then the transfected cells express the recombinant protein.

The present invention provides cell adhesion as one of the modes of monitoring cells' response to stimulus. Many primary science sources report that a plethora of cellular events and responses are linked to one of the several modes of cell adhesion. The present invention describes methods of practice of a biosensor for the monitoring of cell adhesion in native responses to stimulus.

The instant invention provides commercially feasible high-throughput methodologies that can perform high sensitivity cell-based assays without any type of label in a format that is readily compatible with the microtiter plate-based or microarray-based infrastructure that is most often used for high-throughput biomolecular interaction analysis.

DETAILED DESCRIPTION OF THE INVENTION

Figure 1:
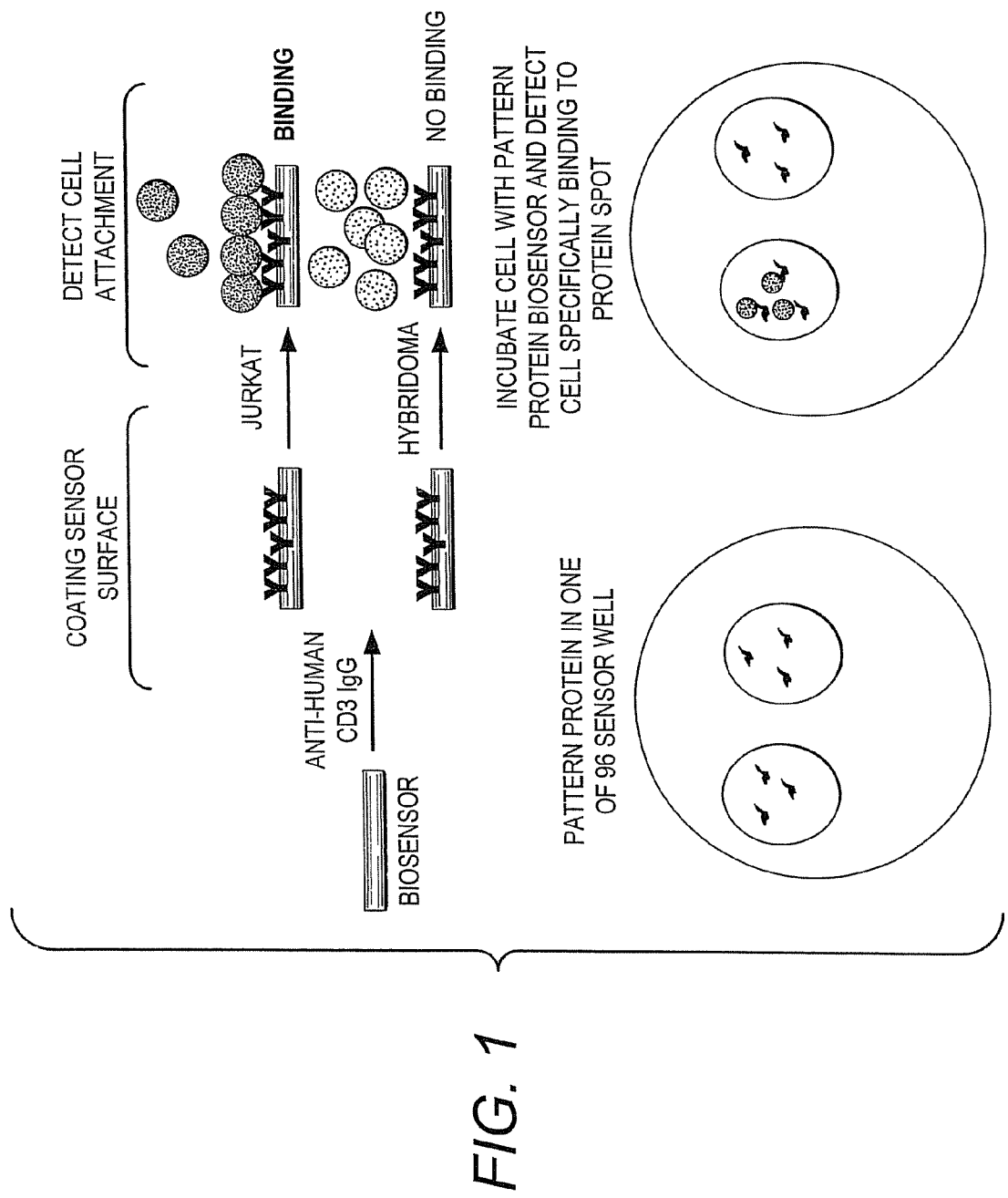
FIG. 1 shows a schematic diagram of at cell-protein interaction assay.

As used herein, the singular forms "a," "an", and "the" include plural referents unless the context clearly dictates otherwise.

Biosensors

Biosensors of the invention can be colorimetric resonant reflectance biosensors. See e.g., Cunningham et al., "Colorimetric resonant reflection as a direct biochemical assay technique," Sensors and Actuators B, Volume 81, p. 316-328, Jan. 5, 2002; U.S. Pat. Publ. No. 2004/0091397; U.S. Pat. Nos. 7,094,595; 7,264,973. Colorimetric resonant biosensors are not surface plasmon resonant (SPR) biosensors. SPR biosensors have a thin metal layer, such as silver, gold, copper, aluminum, sodium, and indium. The metal must have conduction band electrons capable of resonating with light at a suitable wavelength. A SPR biosensor surface exposed to light must be pure metal. Oxides, sulfides and other films interfere with SPR. Colorimetric resonant biosensors do not have a metal layer, rather they have a dielectric coating of high refractive index material, such as zinc sulfide, titanium dioxide, tantalum oxide, and silicon nitride.

Grating-based waveguide biosensors are described in, e.g., U.S. Pat. No. 5,738,825. A grating-based waveguide biosensor comprises a waveguiding film and a diffraction grating that incouples an incident light field into the waveguiding film to generate a diffracted light field. A change in the effective refractive index of the waveguiding film is detected. Devices where the wave must be transported a significant distance within the device, such as grating-based waveguide biosensors, lack the spatial resolution of the current invention.

A colorimetric resonant reflectance biosensor allows biochemical interactions to be measured on the biosensor's surface without the use of fluorescent tags, colorimetric labels or any other type of detection tag or detection label. A biosensor surface contains an optical structure that, when illuminated with collimated and/or white light, is designed to reflect only a narrow band of wavelengths ("a resonant grating effect"). The narrow wavelength band is described as a wavelength "peak." The "peak wavelength value" (PWV) changes when materials, such as biological materials, are deposited or removed from the biosensor surface. A readout instrument is used to illuminate distinct locations on a biosensor surface with collimated and/or white light, and to collect reflected light. The collected light is gathered into a wavelength spectrometer for determination of a PWV.

A biosensor can be incorporated into standard disposable laboratory items such as microtiter plates by bonding the structure (biosensor side up) into the bottom of a bottomless microtiter plate cartridge. Incorporation of a biosensor into common laboratory format cartridges is desirable for compatibility with existing microtiter plate handling equipment such as mixers, incubators, and liquid dispensing equipment. Biosensors can also be incorporated into, e.g., microfluidic, macrofluidic, or microarray devices (see, e.g., U.S. Pat. Nos. 7,033,819, 7,033,821). Biosensors can be used with well-know methodology in the art (see, e.g., *Methods of Molecular Biology* edited by Jun-Lin Guan, Vol. 294, Humana Press, Totowa, N.J.) to monitor cell behavioral changes or the lack of these changes upon exposure to one or more extracellular reagents.

Colorimetric resonant reflectance biosensors comprise subwavelength structured surfaces (SWS) and are an unconventional type of diffractive optic that can mimic the effect of thin-film coatings. (Peng & Morris, "Resonant scattering from two-dimensional gratings," *J. Opt. Soc. Am. A*, Vol. 13, No. 5, p. 993, May 1996; Magnusson, & Wang, "New principle for optical filters," *Appl. Phys. Lett.*, 61, No. 9, p. 1022, August, 1992; Peng & Morris, "Experimental demonstration of resonant anomalies in diffraction from two-dimensional gratings," *Optics Letters*, Vol. 21, No. 8, p. 549, April, 1996). A SWS structure contains a one-dimensional, two-dimensional, or three dimensional grating in which the grating period is small compared to the wavelength of incident light so that no diffractive orders other than the reflected and transmitted zeroth orders are allowed to propagate. Propagation of guided modes in the lateral direction are not supported. Rather, the guided mode resonant effect occurs over a highly localized region of approximately 3 microns from the point that any photon enters the biosensor structure.

The reflected or transmitted light of a colorimetric resonant reflectance biosensor can be modulated by the addition of molecules such as ligands or binding partners or both to the upper surface of the biosensor. The added molecules increase the optical path length of incident radiation through the structure, and thus modify the wavelength at which maximum reflectance or transmittance will occur.

In one embodiment, a colorimetric resonant reflectance biosensor, when illuminated with white and/or collimated light, is designed to reflect a single wavelength or a narrow band of wavelengths (a "resonant grating effect"). When mass is deposited on the surface of the biosensor, the reflected wavelength is shifted due to the change of the optical path of light that is shown on the biosensor.

A detection system consists of, for example, a light source that illuminates a small spot of a biosensor at normal incidence through, for example, a fiber optic probe, and a spectrometer that collects the reflected light through, for example, a second fiber optic probe also at normal incidence. Because no physical contact occurs between the excitation/detection system and the biosensor surface, no special coupling prisms are required and the biosensor can be easily adapted to any commonly used assay platform including, for example, microtiter plates. A single spectrometer reading can be performed in several milliseconds, thus it is possible to quickly measure a large number of molecular interactions taking place in parallel upon a biosensor surface, and to monitor reaction kinetics in real time.

A colorimetric resonant reflectance biosensor comprises, e.g., an optical grating comprised of a high refractive index material, a substrate layer that supports the grating, and optionally one or more specific binding substances or linkers immobilized on the surface of the grating opposite of the substrate layer. The high refractive index material has a higher refractive index than a substrate layer. See, e.g., U.S. Pat. Nos. 7,094,595; 7,070,987. Optionally, a cover layer covers the grating surface. An optical grating is coated with a high refractive index dielectric film which can be comprised of a material that includes, for example, zinc sulfide, titanium dioxide, tantalum oxide, silicon nitride, and silicon dioxide. A cross-sectional profile of a grating with optical features can comprise any periodically repeating function, for example, a "square-wave." An optical grating can also comprise a repeating pattern of shapes selected from the group consisting of lines (one-dimensional), squares, circles, ellipses, triangles, trapezoids, sinusoidal waves, ovals, rectangles, and hexagons. A colorimetric resonant reflectance biosensor of the invention can also comprise an optical grating comprised of, for example, plastic or epoxy, which is coated with a high refractive index material.

Linear gratings (i.e., one dimensional gratings) have resonant characteristics where the illuminating light polarization is oriented perpendicular to the grating period. A colorimetric resonant reflection biosensor can also comprise, for example, a two-dimensional grating, e.g., a hexagonal array of holes or squares. Other shapes can be used as well. A linear grating has the same pitch (i.e. distance between regions of high and low refractive index), period, layer thicknesses, and material properties as a hexagonal array grating. However, light must be polarized perpendicular to the grating lines in order to be resonantly coupled into the optical structure. Therefore, a polarizing filter oriented with its polarization axis perpendicular to the linear grating must be inserted between the illumination source and the biosensor surface. Because only a small portion of the illuminating light source is correctly polarized, a longer integration time is required to collect an equivalent amount of resonantly reflected light compared to a hexagonal grating.

An optical grating can also comprise, for example, a "stepped" profile, in which high refractive index regions of a single, fixed height are embedded within a lower refractive index cover layer. The alternating regions of high and low refractive index provide an optical waveguide parallel to the top surface of the biosensor.

A colorimetric resonant reflectance biosensor of the invention can further comprise a cover layer on the surface of an optical grating opposite of a substrate layer. Where a cover layer is present, the one or more specific binding substances are immobilized on the surface of the cover layer opposite of the grating. Preferably, a cover layer comprises a material that has a lower refractive index than a material that comprises the grating. A cover layer can be comprised of, for example, glass (including spin-on glass (SOG)), epoxy, or plastic.

For example, various polymers that meet the refractive index requirement of a biosensor can be used for a cover layer. SOG can be used due to its favorable refractive index, ease of handling, and readiness of being activated with specific binding substances using the wealth of glass surface activation techniques. When the flatness of the biosensor surface is not an issue for a particular system setup, a grating structure of SiN/glass can directly be used as the sensing surface, the activation of which can be done using the same means as on a glass surface.

Resonant reflection can also be obtained without a planarizing cover layer over an optical grating. For example, a biosensor can contain only a substrate coated with a structured thin film layer of high refractive index material. Without the use of a planarizing cover layer, the surrounding medium (such as air or water) fills the grating. Therefore, specific binding substances are immobilized to the biosensor on all surfaces of an optical grating exposed to the specific binding substances, rather than only on an upper surface.

In general, a colorimetric resonant reflectance biosensor can be illuminated with white and/or collimated light that will contain light of every polarization angle. The orientation of the polarization angle with respect to repeating features in a biosensor grating will determine the resonance wavelength. For example, a "linear grating" (i.e., a one-dimensional grating) biosensor consisting of a set of repeating lines and spaces will have two optical polarizations that can generate separate resonant reflections. Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A biosensor can generally be designed to optimize the properties of only one polarization (the s-polarization), and the non-optimized polarization is easily removed by a polarizing filter.

In order to remove the polarization dependence, so that every polarization angle generates the same resonant reflection spectra, an alternate biosensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single sensor location—such as an array spot or a microtiter plate well. Each separate microarray spot or microtiter plate well has a separate concentric ring pattern centered within it. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron. The grating depth is about 0.01 to about 1 micron.

In another embodiment, an array of holes or posts are arranged to closely approximate the concentric circle structure described above without requiring the illumination beam to be centered upon any particular location of the grid. Such an array pattern is automatically generated by the optical interference of three laser beams incident on a surface from three directions at equal angles. In this pattern, the holes (or posts) are centered upon the corners of an array of closely packed hexagons. The holes or posts also occur in the center of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron.

A detection system can comprise a colorimetric resonant reflectance biosensor a light source that directs light to the colorimetric resonant reflectance biosensor, and a detector that detects light reflected from the biosensor. In one embodiment, it is possible to simplify the readout instrumentation by the application of a filter so that only positive results over a determined threshold trigger a detection.

By measuring the shift in resonant wavelength at each distinct location of a colorimetric resonant reflectance biosensor of the invention, it is possible to determine which distinct locations have, e.g., biological material deposited on them. The extent of the shift can be used to determine, e.g., the amount of binding partners in a test sample and the chemical affinity between one or more specific binding substances and the binding partners of the test sample.

A colorimetric resonant reflectance biosensor can be illuminated twice. The first measurement determines the reflectance spectra of one or more distinct locations of a biosensor with, e.g., no biological material on the biosensor. The second measurement determines the reflectance spectra after, e.g., one or more cells are applied to a biosensor. The difference in peak wavelength between these two measurements is a measurement of the presence or amount of cells on the biosensor. This method of illumination can control for small imperfections in a surface of a biosensor that can result in regions with slight variations in the peak resonant wavelength. This method can also control for varying concentrations or density of cell matter on a biosensor.

Surface of Biosensor

Immobilization of one or more ligands onto a biosensor is performed so that a ligand will not be washed away by any rinsing procedures, and so that the binding of the ligand to binding partners in a test sample is unimpeded by the biosensor surface. One or more ligands can be attached to a biosensor surface by physical adsorption (i.e., without the use of chemical linkers) or by chemical binding (i.e., with the use of chemical linkers) as well as electrochemical binding, electrostatic binding, hydrophobic binding and hydrophilic binding. Chemical binding can generate stronger attachment of ligands on a biosensor surface and provide defined orientation and conformation of the surface-bound molecules.

A ligand can also be specifically bound to a biosensor surface via a specific binding substance such as a nucleic acid, peptide, protein solution, peptide solution, solutions containing compounds from a combinatorial chemical library, antigen, polyclonal antibody, monoclonal antibody, single chain antibody (scFv), F(ab) fragment, F(ab')$_2$ fragment, Fv fragment, small organic molecule, virus, polymer or biological sample, wherein the specific binding substance is immobilized to the surface of the biosensor.

Furthermore, ligands can be arranged in an array of one or more distinct locations on the biosensor surface, said surface residing within one or more wells of a multiwell plate and comprising one or more surfaces of the multiwell plate or microarray. The array of ligands comprises one or more ligands on the biosensor surface within a microwell plate such that a surface contains one or more distinct locations, each with a different ligand For example, an array can comprise 1, 10, 100, 1,000, 10,000 or 100,000 or greater distinct locations. Thus, each well of a multiwell plate or microarray can have within it an array of one or more distinct locations separate from the other wells of the multiwell plate, which allows multiple different samples to be processed on one multiwell plate. The array or arrays within any one well can be the same or different than the array or arrays found in any other microtiter wells of the same microtiter plate.

Immobilization of a ligand to a biosensor surface can be also be affected via binding to, for example, the following functional linkers: a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. Furthermore, a ligand can be immobilized on the surface of a biosensor via physical adsorption, chemical binding, electrochemical binding, electrostatic binding, hydrophobic binding or hydrophilic binding, and immunocapture methods.

In one embodiment of the invention a biosensor can be coated with a linker such as, e.g., a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. For example, an amine surface can be used to attach several types of linker molecules while an aldehyde surface can be used to bind proteins directly, without an additional linker. A nickel surface can be used to bind molecules that have an incorporated histidine ("his") tag. Detection of "his-tagged" molecules with a nickel-activated surface is well known in the art (Whitesides, *Anal. Chem.* 68, 490, (1996)).

Linkers, ligands, and specific binding substances can be immobilized on the surface of a biosensor such that each well has the same linker, ligands, and/or specific binding substances immobilized therein. Alternatively, each well can contain a different combination of linkers, ligands, and/or specific binding substances.

A ligand can specifically or non-specifically bind to a linker or specific binding substance immobilized on the surface of a biosensor. Alternatively, the surface of the biosensor can have no linker or specific binding substance and a ligand can bind to the biosensor surface non-specifically.

Immobilization of one or more specific binding substances or linker onto a biosensor is performed so that a specific binding substance or linker will not be washed away by rinsing procedures, and so that its binding to ligand in a test sample is unimpeded by the biosensor surface. Several different types of surface chemistry strategies have been implemented for covalent attachment of specific binding substances to, for example, glass for use in various types of microarrays and biosensors. These same methods can be readily adapted to a biosensor of the invention. Surface preparation of a biosensor so that it contains the correct functional groups for binding one or more specific binding substances is an integral part of the biosensor manufacturing process.

One or more specific ligands can be attached to a biosensor surface by physical adsorption (i.e., without the use of chemical linkers) or by chemical binding (i.e., with the use of chemical linkers) as well as electrochemical binding, electrostatic binding, hydrophobic binding and hydrophilic binding. Chemical binding can generate stronger attachment of ligands on a biosensor surface and provide defined orientation and conformation of the surface-bound molecules.

Immobilization of ligands to plastic, epoxy, or high refractive index material can be performed essentially as described for immobilization to glass. However, the acid wash step can be eliminated where such a treatment would damage the material to which the specific binding substances are immobilized.

Ligands

A ligand is a molecule that binds to another molecule. Ligand and specific binding substance are analogous terms. A ligand can be, for example, a nucleic acid, peptide, extracellular matrix ligand (see Table 1), protein solutions, peptide solutions, single or double stranded DNA solutions, RNA solutions, RNA-DNA hybrid solutions, solutions containing compounds from a combinatorial chemical library, antigen, polyclonal antibody, monoclonal antibody, single chain antibody (scFv), F(ab) fragment, F(ab')$_2$ fragment, Fv fragment, small organic molecule, cell, virus, bacteria, polymer or biological sample. A biological sample can be for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatic fluid. The polymer is selected from the group of long chain molecules with multiple active sites per molecule consisting of hydrogel, dextran, poly-amino acids and derivatives thereof, including poly-lysine (comprising poly-l-lysine and poly-d-lysine), poly-phe-lysine and poly-glu-lysine. In one embodiment of the invention, ligands are extracellular matrix protein ligands.

Preferably, one or more ligands are arranged in an array of one or more distinct locations on a biosensor. An array of ligands comprises one or more ligands on a surface of a biosensor of the invention such that a surface contains many distinct locations, each with a different ligand or with a different amount of ligands. For example, an array can comprise 1, 10, 100, 1,000, 10,000 or 100,000 distinct locations. Such a biosensor surface is called an array because one or more ligands are typically laid out in a regular grid pattern in x-y coordinates. However, an array of the invention can comprise one or more ligands in any type of regular or irregular pattern. For example, distinct locations can define an array of spots of one or more ligands. An array spot can be about 50 to about 500 microns in diameter. An array spot can also be about 150 to about 200 microns in diameter. One or more ligands can be bound to their specific receptors.

An array on a biosensor of the invention can be created by placing microdroplets of one or more ligands onto, for example, an x-y grid of locations on a grating or cover layer surface. When the biosensor is exposed to a test sample comprising one or more binding partners, e.g., cells having receptors for ligands, the binding partners will be preferentially attracted to distinct locations on the microarray that comprise ligands that have high affinity for the binding partners. Some of the distinct locations will gather binding partners onto their surface, while other locations will not.

A ligand specifically binds to a binding partner that is added to the surface of a biosensor of the invention. A ligand specifically binds to its binding partner, but does not substantially bind other binding partners added to the surface of a biosensor. For example, where the ligand is an antibody and its binding partner is a particular antigen, the antibody specifically binds to the particular antigen, but does not substantially bind other antigens. A binding partner can be, for example, a nucleic acid, peptide, protein solutions, peptide solutions, extracellular matrix protein receptor, an integrin (see Table 1), single or double stranded DNA solutions, RNA solutions, RNA-DNA hybrid solutions, solutions containing compounds from a combinatorial chemical library, antigen, polyclonal antibody, monoclonal antibody, single chain antibody (scFv), F(ab) fragment, F(ab')$_2$ fragment, Fv fragment, small organic molecule, cell, virus, bacteria, polymer or biological sample. A biological sample can be, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, and prostatic fluid. In one embodiment of the invention a binding partner is a receptor that can bind a ligand immobilized on the biosensor, wherein the receptor is on the surface of a cell.

While microtiter plates are the most common format used for biochemical assays, microarrays are increasingly seen as a means for maximizing the number of biochemical interactions that can be measured at one time while minimizing the volume of precious reagents. By application of ligands with a microarray spotter onto a biosensor of the invention, ligand densities of 10,000 ligands/in$^2$ can be obtained. By focusing an illumination beam to interrogate a single microarray location, a biosensor can be used as a label-free microarray readout system.

Further, both the microarray and microtiter plate embodiments can be combined such that one or more ligands are arranged in an array of one or more distinct locations on the biosensor surface, said surface residing within one or more wells of the microtiter plate and comprising one or more surfaces of the microtiter plate, preferably the bottom surface. The array of ligands comprises one or more ligands on the sensor surface within a microtiter plate well such that a surface contains one or more distinct locations, each with different ligands or with a different amount of a ligands For example, an array can comprise 1, 10, 100, 1,000, 10,000 or 100,000 distinct locations. Thus, each well of the microtiter plate embodiment can have within it an array of one or more distinct locations separate from the other wells of the microtiter plate embodiment, which allows multiple different samples to be processed on one microtiter plate of the invention, one or more samples for each separate well. The array or arrays within any one well can be the same or different than the array or arrays found in any other microtiter wells of the same microtiter plate.

Liquid-Containing Vessels

A grating of the invention can comprise an inner surface, for example, a bottom surface of a liquid-containing vessel. A liquid-containing vessel can be, for example, a microtiter plate well, a test tube, a petri dish, or a microfluidic channel. One embodiment of this invention is a biosensor that is incorporated into any type of microtiter plate. For example, a biosensor can be incorporated into the bottom surface of a microtiter plate by assembling the walls of the reaction vessels over the biosensor surface, so that each reaction "spot" can be exposed to a distinct test sample. Therefore, each individual microtiter plate well can act as a separate reaction vessel. Separate chemical reactions can, therefore, occur within adjacent wells without intermixing reaction fluids and chemically distinct test solutions can be applied to individual wells.

Several methods for attaching a biosensor or grating of the invention to the bottom surface of bottomless microtiter plates can be used, including, for example, adhesive attachment, ultrasonic welding, and laser welding.

The most common assay formats for pharmaceutical high-throughput screening laboratories, molecular biology research laboratories, and diagnostic assay laboratories are microtiter plates. The plates are standard-sized plastic cartridges that can contain about 2, 6, 8, 24, 48, 96, 384, 1536, 3456, 9600 or more individual reaction vessels arranged in a grid. Due to the standard mechanical configuration of these plates, liquid dispensing, robotic plate handling, and detection systems are designed to work with this common format. A biosensor of the invention can be incorporated into the bottom surface of a standard microtiter plate. Because the biosensor surface can be fabricated in large areas, and because the readout system does not make physical contact with the biosensor surface, an arbitrary number of individual biosensor areas can be defined that are only limited by the focus resolution of the illumination optics and the x-y stage that scans the illumination/detection probe across the biosensor surface.

Methods of Using Biosensors

Biosensors of the invention can be used to study one or a number of ligand/binding partner interactions in parallel. Binding of one or more ligands to their respective binding partners can be detected, without the use of labels, by applying one or more binding partners to a biosensor that have one or more ligands immobilized on their surfaces. In one embodiment of the invention, one or more ligands are one or more extracellular matrix protein ligands and the one or more binding partners are receptors on cells, wherein the receptors (e.g., an integrin) are specific for extracellular matrix protein ligands. A biosensor is illuminated with light and a maxima in reflected wavelength, or a minima in transmitted wavelength of light is detected from the biosensor. Signals are detected from a grating-based waveguide biosensor and are compared to each other or to controls in a manner similar to that for colorimetric resonant reflectance biosensors. All assays or methods described herein can be performed on colorimetric resonant reflectance biosensors and grating-based waveguide biosensor. If one or more ligands have bound to their respective binding partners, then the reflected wavelength of light is shifted as compared to a situation where one or more ligands have not bound to their respective binding partners. Where a biosensor is coated with an array of one or more distinct locations containing the one or more ligands, then a maxima in reflected wavelength or minima in transmitted wavelength of light is detected from each distinct location of the biosensor.

In one embodiment of the invention, a variety of ligands, for example, ECM ligands, can be immobilized in an array format onto a biosensor of the invention. The biosensor is then contacted with a test sample of interest comprising binding partners, such as cells bearing ECM ligand receptors, e.g., integrins or focal adhesion proteins. Only the cells that specifically bind to the ligands are immobilized on the biosensor. Once bound, the cells respond to stimuli unlike unbound cells. The use of an enzyme or fluorescent label is not required. For high-throughput applications, biosensors can be arranged in an array of arrays, wherein several biosensors comprising an array of specific binding substances are arranged in an array. Such an array of arrays can be, for example, dipped into microtiter plate to perform many assays at one time. In another embodiment, a biosensor can occur on the tip of a fiber probe for in vivo detection of biochemical substance. Alternatively, cells can be mixed with ECM ligands or be derived as a mixture of cells and ECM and then added to a biosensor surface.

One embodiment of the invention allows the direct detection of cell changes, such as changes in cell growth patterns, cell death patterns, changes in cell movement, changes in cell size or volume, or changes in cell adhesion, as they occur in real time with a colorimetric resonant reflectance biosensor or grating based waveguide biosensor and without the need to incorporate or without interference from radiometric, colorimetric, or fluorescent labels (although labels may be used if desired). Changes in cell behavior and morphology can be detected as the cell is perturbed. The cellular changes can then be detected in real time using a high speed, high resolution instrument, such as the BIND Scanner™ (i.e., a colorimetric resonant reflectance biosensor system), and corresponding algorithms to quantify data. See, e.g., U.S. Pat. No. 6,951,715 and U.S. Pat. Publ. 2004/0151626. By combining this methodology, instrumentation and computational analysis, cellular behavior can be expediently monitored in real time (i.e., expediently and conveniently observing and quantifying cell reactions during the instant the cell is responding to stimulus and over time while the cell is responding to the stimulus), in a label free manner.

Colorimetric resonant reflectance biosensors, such as SRU Biosystems, Inc. BIND™ technology (Woburn, Mass.) have the capability of measuring changes to a surface with respect to mass attachment from nanoscale biological systems. The applications and the methods, in which colorimetric resonant reflectance biosensors have been previously implemented, have changed as the resolution of the instruments has improved. Previously, measurement of the quantity of cells attached to the colorimetric resonant reflectance biosensor surface was the primary goal. While looking at some poorer resolution images of cells, however, it was noted that cells gave differential signals with respect to the number of pixels occupied, intensity of signal/pixel, change in PWV of each pixel, etc. While trying to reduce the variability of these data, it became clear that the variability lay within the individual cells and their differential morphological responses to stimuli. To further investigate these cellular events, a higher resolution version of a BIND Scanner™ (i.e., a colorimetric resonant reflectance biosensor system), was constructed. The scanner has a higher resolution lens than previously used scanners. The lens has a resolution of about 2-5, 2-10, 2-15, 2-20, 2-50, 2-100, 2-200 or 2-300, micrometers. Additionally, a methodology was developed for analyzing cell changes in real time at better resolution.

Another embodiment of the invention provides a method of detecting cell migration and chemotaxis. In particular, cells can be grown on one end of a colorimetric resonant reflectance optical biosensor, either within a well or in an array format. The end of the biosensor containing the cells can optionally be segregated, via the use of semi-permeable membranes or microfluidic channels, from the opposing end where the chemotactic agent is placed. Detection systems comprised of an imaging spectrometer, or alternatively a fiber optic probe that can be moved to read from multiple locations of the biosensor, can then be used to detect the location of the cells, and in turn permit the computation of the cell migration velocity.

A further embodiment of the invention provides a method of detecting a change in cell growth patterns. Briefly, cells can be grown on a colorimetric resonant reflectance optical biosensor; a PWV detected; a test reagent applied to the cells; a PWV detected; and the initial PWV with the subsequent PWV can be compared, wherein the difference between the initial PWV in relation to the subsequent PWV indicates a change in cell growth patterns. A difference in PWV correlates with a change in a cell growth pattern.

The change in cell growth pattern can be selected from the group consisting of cell morphology, cell adhesion, cell migration, cell proliferation and cell death. One type of prokaryotic or eukaryotic cells or two or more types of eukaryotic or prokaryotic cells can be grown on the biosensor. The biosensor can comprise an internal surface of a vessel selected from the group consisting of a microtiter well, microtiter plate, test tube, petri dish and microfluidic channel.

Biosensors of the invention are also capable of detecting and quantifying the amount of a binding partner from a sample that is bound to one or more distinct locations defining an array by measuring the shift in reflected wavelength of light. For example, the wavelength shift at one or more distinct locations can be compared to positive and negative controls at other distinct locations to determine the amount of a specific binding substance that is bound. Importantly, numerous such one or more distinct locations can be arranged on the biosensor surface, and the biosensor can comprise an internal surface of a vessel such as an about 2, 6, 8, 24, 48, 96, 384, 1536, 3456, 9600 or more well-microtiter plate. As an example, where 96 biosensors are attached to a holding fixture and each biosensor comprises about 100 distinct locations, about 9600 biochemical assays can be performed simultaneously.

Detection Systems

A detection system can comprise a biosensor a light source that directs light to the biosensor, and a detector that detects light reflected from the biosensor. In one embodiment, it is possible to simplify the readout instrumentation by the application of a filter so that only positive results over a determined threshold trigger a detection.

A light source can illuminate a colorimetric resonant reflectance biosensor from its top surface, i.e., the surface to which one or more specific binding substances are immobilized or from its bottom surface. By measuring the shift in resonant wavelength at each distinct location of a biosensor of the invention, it is possible to determine which distinct locations have binding partners bound to them. The extent of the shift can be used to determine the amount of binding partners in a test sample and the chemical affinity between one or more specific binding substances and the binding partners of the test sample.

A biosensor can be illuminated twice. The first measurement determines the reflectance spectra of one or more distinct locations of a biosensor array with one or more specific binding substances immobilized on the biosensor. The second measurement determines the reflectance spectra after one or more binding partners are applied to a biosensor. The difference in peak wavelength between these two measurements is a measurement of the amount of binding partners that have specifically bound to a biosensor or one or more distinct locations of a biosensor. This method of illumination can control for small nonuniformities in a surface of a biosensor that can result in regions with slight variations in the peak resonant wavelength. This method can also control for varying concentrations or molecular weights of specific binding substances immobilized on a biosensor.

One type of detection system for illuminating the biosensor surface and for collecting the reflected light is a probe containing, for example, six illuminating optical fibers that are connected to a light source, and a single collecting optical fiber connected to a spectrometer. The number of fibers is not critical, any number of illuminating or collecting fibers are possible. The fibers are arranged in a bundle so that the collecting fiber is in the center of the bundle, and is surrounded by the six illuminating fibers. The tip of the fiber bundle is connected to a collimating lens that focuses the illumination onto the surface of the biosensor.

In this probe arrangement, the illuminating and collecting fibers are side-by-side. Therefore, when the collimating lens is correctly adjusted to focus light onto the biosensor surface, one observes six clearly defined circular regions of illumination, and a central dark region. Because the biosensor does not scatter light, but rather reflects a collimated beam, no light is incident upon the collecting fiber, and no resonant signal is observed. Only by defocusing the collimating lens until the six illumination regions overlap into the central region is any light reflected into the collecting fiber. Because only defocused, slightly uncollimated light can produce a signal, the biosensor is not illuminated with a single angle of incidence, but with a range of incident angles. The range of incident angles results in a mixture of resonant wavelengths. Thus, wider resonant peaks are measured than might otherwise be possible.

Therefore, it is desirable for the illuminating and collecting fiber probes to spatially share the same optical path. Several methods can be used to co-locate the illuminating and collecting optical paths. For example, a single illuminating fiber, which is connected at its first end to a light source that directs light at the biosensor, and a single collecting fiber, which is connected at its first end to a detector that detects light reflected from the biosensor, can each be connected at their second ends to a third fiber probe that can act as both an illuminator and a collector. The third fiber probe is oriented at a normal angle of incidence to the biosensor and supports counter-propagating illuminating and reflecting optical signals.

Another method of detection involves the use of a beam splitter that enables a single illuminating fiber, which is connected to a light source, to be oriented at a 90 degree angle to a collecting fiber, which is connected to a detector. Light is directed through the illuminating fiber probe into the beam splitter, which directs light at the biosensor. The reflected light is directed back into the beam splitter, which directs light into the collecting fiber probe. A beam splitter allows the illuminating light and the reflected light to share a common optical path between the beam splitter and the biosensor, so perfectly collimated light can be used without defocusing.

Angular Scanning

Detection systems of the invention are based on collimated white light illumination of a biosensor surface and optical spectroscopy measurement of the resonance peak of the reflected beam. Molecular binding on the surface of a biosensor is indicated by a shift in the peak wavelength value, while an increase in the wavelength corresponds to an increase in molecular absorption.

As shown in theoretical modeling and experimental data, the resonance peak wavelength is strongly dependent on the incident angle of the detection light beam. Because of the angular dependence of the resonance peak wavelength, the incident white light needs to be well collimated. Angular dispersion of the light beam broadens the resonance peak, and reduces biosensor detection sensitivity. In addition, the signal quality from the spectroscopic measurement depends on the power of the light source and the sensitivity of the detector. In order to obtain a high signal-to-noise ratio, an excessively long integration time for each detection location can be required, thus lengthening overall time to readout a biosensor plate. A tunable laser source can be used for detection of grating resonance, but is expensive.

In one embodiment of the invention, these disadvantages are addressed by using a laser beam for illumination of a biosensor, and a light detector for measurement of reflected beam power. A scanning mirror device can be used for varying the incident angle of the laser beam, and an optical system is used for maintaining collimation of the incident laser beam. See, e.g., "Optical Scanning" (Gerald F. Marchall ed., Marcel Dekker (1991). Any type of laser scanning can be used. For example, a scanning device that can generate scan lines at a rate of about 2 lines to about 1,000 lines per second is useful in the invention. In one embodiment of the invention, a scanning device scans from about 50 lines to about 300 lines per second.

In one embodiment, the reflected light beam passes through part of the laser scanning optical system, and is measured by a single light detector. The laser source can be a diode laser with a wavelength of, for example, 780 nm, 785 nm, 810 nm, or 830 nm. Laser diodes such as these are readily available at power levels up to 150 mW, and their wavelengths correspond to high sensitivity of Si photodiodes. The detector thus can be based on photodiode biosensors. A light source provides light to a scanner device, which directs the light into an optical system. The optical system directs light to a biosensor. Light is reflected from the biosensor to the optical system, which then directs the light into a light signal detector. In one embodiment as the scanning mirror changes its angular position, the incident angle of the laser beam on the surface changes by nominally twice the mirror angular displacement. The scanning mirror device can be a linear galvanometer, operating at a frequency of about 2 Hz up to about 120 Hz, and mechanical scan angle of about 10 degrees to about 20 degrees. In this example, a single scan can be completed within about 10 msec. A resonant galvanometer or a polygon scanner can also be used. A simple optical system for angular scanning can consist of a pair of lenses with a common focal point between them. The optical system can be designed to achieve optimized performance for laser collimation and collection of reflected light beam.

The angular resolution depends on the galvanometer specification, and reflected light sampling frequency. Assuming galvanometer resolution of 30 arcsec mechanical, corresponding resolution for biosensor angular scan is 60 arcsec, i.e. 0.017 degree. In addition, assume a sampling rate of 100 ksamples/sec, and 20 degrees scan within 10 msec. As a result, the quantization step is 20 degrees for 1000 samples, i.e. 0.02 degree per sample. In this example, a resonance peak width of 0.2 degree, as shown by Peng and Morris (Experimental demonstration of resonant anomalies in diffraction from two-dimensional gratings, *Optics Lett.*, 21:549 (1996)), will be covered by 10 data points, each of which corresponds to resolution of the detection system.

The advantages of such a detection system includes: excellent collimation of incident light by a laser beam, high signal-to-noise ratio due to high beam power of a laser diode, low cost due to a single element light detector instead of a spectrometer, and high resolution of resonance peak due to angular scanning.

Cell Adhesion and Cell Response Assays

Integrins are cell surface receptors that interact with the extracellular matrix (ECM) and mediate intracellular signals. Integrins are responsible for cytoskeletal organization, cellular motility, regulation of the cell cycle, regulation of cellular of integrin affinity, attachment of cells to viruses, attachment of cells to other cells or ECM. Integrins are also responsible for signal transduction, a process whereby the cell transforms one kind of signal or stimulus into another intracellularly and intercellularly. Integrins can transduce information from the ECM to the cell and information from the cell to other cells (e.g., via integrins on the other cells) or to the ECM. A list of integrins and their ECM ligands can be found in Takada et al., Genome Biology 8:215 (2007) as shown in Table 1.

TABLE 1

| Integrin | ECM ligand |
|---|---|
| $\alpha_1\beta_1$ | Laminin, collagen |
| $\alpha_2\beta_1$ | Laminin, collagen, thrombospondin, E-cadherin, tenascin |
| $\alpha_3\beta_1$ | Laminin, thrombospondin, uPAR |
| $\alpha_4\beta_1$ | Thrombospondin, MadCAM-1, VCAM-1, fibronectin, osteopontin, ADAM, ICAM-4 |
| $\alpha_5\beta_1$ | Fibronectin, osteopontin, fibrillin, thrombospondin, ADAM, COMP, L1 |
| $\alpha_6\beta_1$ | Laminin, thrombospondin, ADAM, Cyr61 |
| $\alpha_7\beta_1$ | Laminin |
| $\alpha_8\beta_1$ | Tenascin, fibronectin, osteopontin, vitronectin, LAP-TGF-β, nephronectin, |
| $\alpha_9\beta_1$ | Tenascin, VCAM-1, osteopontin, uPAR, plasmin, angiostatin, ADAM, VEGF-C, VEGF-D |
| $\alpha_{10}\beta_1$ | Laminin, collegen |
| $\alpha_{11}\beta_1$ | Collagen |
| $\alpha v\beta_1$ | LAP-TGF-β, fibronectin, osteopontin, L1 |
| $\alpha L\beta_2$ | ICAM, ICAM-4 |
| $\alpha M\beta_2$ | ICAM, iC3b, factor X, fibrinogen, ICAM-4, heparin |
| $\alpha X\beta_2$ | ICAM, iC3b, fibrinogen, ICAM-4, heparin, collagen |

TABLE 1-continued

| Integrin | ECM ligand |
|---|---|
| $\alpha D\beta_2$ | ICAM, VCAM-1, fibrinogen, fibronectin, vitronectin, Cyr61, plasminogen |
| $\alpha_{IIb}\beta_3$ | Fibrinogen, thrombospondin, fibronectin, vitronectin, vWF, Cyr61, ICAM-4, L1, CD40 ligand |
| $\alpha v\beta_3$ | Fibrinogen, vitronectin, vWF, thrombospondin, fibrillin, tenascin, PECAM-1, fibronectin, osteopontin, BSP, MFG-E8, ADAM-15, COMP, Cyr61, ICAM-4, MMP, FGF-2, uPA, uPAR. L1, angiostatin, plasmin, cardiotoxin, LAP-TGF-β, Del-1 |
| $\alpha_6\beta_4$ | Laminin |
| $\alpha v\beta_5$ | Osteopontin, BSP, vitronectin, CCN3 [35], LAP-TGF-β |
| $\alpha v\beta_6$ | LAP-TGF-β, fibronectin, osteopontin, ADAM |
| $\alpha_4\beta_7$ | MAdCAM-1, VCAM-1, fibronectin, osteopontin |
| $\alpha E\beta_7$ | E-cadherin |
| $\alpha v\beta_8$ | LAP-TGF-β |

Abbreviations:
ADAM, a disintegrin metalloprotease;
BSP, bone sialic protein;
CCN3, an extracellular matrix protein;
COMP, cartilage oligomeric matrix protein,
Cyr61, cysteine-rich protein 61;
L1, CD171; LAP-TGF-β latency-associated peptide;
iC3b, inactivated complement component 3;
PECAM-1, platelet and endothelial cell adhesion molecule 1;
uPA, urokinase;
uPAR, urokinase receptor;
VEGF, vascular endothelial growth factor;
vWF, von Willebrand Factor.

Other cell surface receptors that interact with the ECM include focal adhesion proteins. Focal adhesion proteins. Focal adhesion proteins form large complexes that connect the cytoskeleton of a cell to the ECM. Focal adhesion proteins include, for example, talin, α-actinin, filamin, vinculin, focal adhesion kinase, paxilin, parvin, actopaxin, nexilin, fimbrin, G-actin, vimentin, syntenin, and many others.

Yet other cell surface receptors can include, but are not limited to those that can interact with the ECM include cluster of differentiation (CD) molecules. CD molecules act in a variety of ways and often act as receptors or ligands for the cell. Other cell surface receptors that interact with ECM include cadherins, adherins, and selectins.

The ECM has many functions including providing support and anchorage for cells, segregation of tissue from one another, and regulation of intracellular communications. The ECM is composed of fibrous proteins and glycosaminoglycans. Glycosaminoglycans are carbohydrate polymers that are usually attached to the ECM proteins to form proteoglycans (including, e.g., heparin sulfate proteoglycans, chondroitin sulfate proteoglycans, karatin sulfate proteoglycans). A glycosaminoglycan that is not found as a proteoglycan is hyaluronic acid. ECM proteins include, for example, collagen (including fibrillar, facit, short chain, basement membrane and other forms of collagen), fibronectin, elastin, and laminin (see Table 1 for additional examples of ECM proteins). ECM ligands useful herein include ECM proteins, glycosaminoglycans, proteoglycans, and hyaluronic acid.

"Specifically binds," "specifically bind" or "specific for" means that a cell surface receptor, e.g., an integrin or focal adhesion protein, etc., binds to a cognate extracellular matrix ligand, with greater affinity than to other, non-specific molecules. A non-specific molecule does not substantially bind to the cell receptor. For example, the integrin α4/β1 specifically binds the ECM ligand fibronectin, but does not specifically bind the non-specific ECM ligands collagen or laminin. In one embodiment of the invention, specific binding of a cell surface receptor to an extracellular matrix ligand, wherein the extracellular matrix ligand is immobilized to a surface, e.g., a biosensor surface, will immobilize the cell to the extracellular matrix ligand and therefore to the surface such that the cell is not washed from the surface by normal cell assay washing procedures.

One embodiment of the invention provides for the use of colorimetric resonant reflection biosensor technology or other biosensor technology, including for example, grating based waveguide biosensor technology, to measure the specific recognition of cell surface receptors for their cognate ECM ligands, wherein the ECM ligands are immobilized on a biosensor surface. By specifically immobilizing cells to a biosensor surface through binding of cell surface receptors, such as integrins, to ECM ligands that are immobilized to the biosensor, the binding of the cells to the biosensor and the cells' response to stimuli is dramatically altered as compared to cells that are non-specifically immobilized to a biosensor surface. That is, detection of response of cells to stimuli is greatly enhanced or augmented where cells are immobilized to a biosensor via ECM ligand binding. In one embodiment of the invention, the cells are in a serum-free medium. A serum-free medium contains about 10, 5, 4, 3, 2, 1, 0.5% or less serum. A serum-free medium can comprise about 0% serum or about 0% to about 1% serum. In one embodiment of the invention cells are added to a biosensor surface where one or more types of ECM ligands have been immobilized to the biosensor surface. In another embodiment of the invention, cells are combined with one or more types of ECM ligands and then added to the surface of a biosensor.

In one embodiment of the invention, an ECM ligand is purified. A purified ECM ligand is an ECM ligand preparation that is substantially free of cellular material, other types of ECM ligands, chemical precursors, chemicals used in preparation of the ECM ligand, or combinations thereof. An ECM ligand preparation that is substantially free of other types of ECM ligands, cellular material, culture medium, chemical precursors, chemicals used in preparation of the ECM ligand, etc., has less than about 30%, 20%, 10%, 5%, 1% or more of other ECM ligands, culture medium, chemical precursors, and/or other chemicals used in preparation. Therefore, a purified ECM ligand is about 70%, 80%, 90%, 95%, 99% or more pure. A purified ECM ligand does not include unpurified or semi-purified preparations or mixtures of ECM ligands that are less than 70% pure, e.g., fetal bovine serum. In one embodiment of the invention, ECM ligands are not purified and comprise a mixture of ECM proteins and non-ECM proteins. Examples of non-purified ECM ligand preparations include fetal bovine serum, bovine serum albumin, and ovalbumin.

For example, cells expressing α4/β1 integrin receptors, which are known to bind to fibronectin ligands, but not to collagen or laminin ligands, generate a PWV shift on fibronectin coated wells that is about 8 to 10 times greater than the PWV shift observed on collagen or laminin surfaces. PWV shifts for cells expressing α4/β1 integrin receptors on biosensor surfaces having collagen or laminin immobilized to them resembles background cell attachment signal observed on BSA-coated control wells.

In one embodiment of the invention detection of cell binding to ECM ligands is increased by about 2, 3, 4, 5, 6, 7, 8, 9, 10, 15, 20 or more times (or any range between 2 and 20 times) when the ECM ligand is specific for a cell surface receptor, e.g., an integrin or focal adhesion protein, present on the surface of the cells. In another embodiment of the invention detection of cellular responses to stimuli is increased by about 2, 3, 4, 5, 6, 7, 8, 9, 10, 15, 20 or more times (or any range between 2 and 20 times) when the cell is immobilized to the biosensor surface by an ECM ligand that is specific for a cell surface receptor, e.g., an integrin.

In a specific example, the lack of cell receptor engagement of cells to a ECM ligands immobilized to the biosensor surface can result in the cells coming into physical contact with the biosensor and adhering nonspecifically onto the biosensor. However, due to the lack of specific cell receptor/ECM ligand binding, no binding or stimulus response or a substantially reduced binding or stimulus (e.g., a shift in PWV) is detected. By optimizing conditions that lead to activation of cell surface receptors the present invention can engage binding of cell surface receptors, such as integrins, to their ECM ligands at increasing levels. Optimization can be done by testing different ECM for adhesion-signaling of the cell using different buffer conditions (e.g., pH, salt, cell nutrients). Cell density within the test apparatus is tested and cell health is assessed for possession of adhesion capability. These methods are well known to those of skill in the art of cell health and culturing maintenance. This optimization results in increasing signal of the cell response to different stimuli such as GPCR, cytokines, or chemokines.

Specific binding of living cells to ECM ligands on biosensors and the responses of cells to stimuli can be detected by methods of the invention. An assay of the invention can involve, e.g., immobilizing one or more ECM ligands on the surface of the biosensor, which can be, for example, $TiO_2$-coated polystyrene, wherein the biosensor is present as a bottom surface of one or more microplate wells. Any part of the surface of the biosensor that is not coated with $TiO_2$ can be blocked with, e.g., ovalbumin or bovine serum albumin (BSA). In one embodiment of the invention, combinations of one or more ECM ligands together with ovalbumin or BSA are added to the biosensor surface and dried for storage. The biosensor can then be rewetted for use in an assay at a later time. For example, fibronectin, laminin and collagen could be combined with ovalbumin, applied to a biosensor and dried for storage. Alternatively, combinations of polypeptides known to bind different integrins, such as RGD (Arg-Gly-Asp) proteins that bind the α-4/β-1 integrin can be immobilized on the surface of the biosensor with ovalbumin or FBS and dried for later use. Other polypeptides know to bind different integrins include the GFOGER proteins found in collagen that bind α11/β1 integrins and DGEA proteins found in collagen.

Cells are added to the surface and optionally incubated for a period of time. Cells can optionally be added to the biosensor in the presence of an adhesion modulator. An adhesion modulator can increase or decrease the ability of the cells to adhere to the biosensor surface and can be, for example, one or more antibodies, metals, integrins, ECM ligands, small organic molecules, proteins, or cell receptor proteins. Cells that do not bind to the surface can be washed away if discrimination of bound from unbound cells is done by eye. Washing of unbound cells from the surface is not necessary if discrimination of bound from unbound cells is done using a biosensor. Bound cells can be detected by colorimetric, luminescent, fluorescent, or other means. The bound cells can be quantified by cell number or mass.

Any type of biosensor can be used in the methods of the invention. Where a colorimetric resonant reflectance biosensor is used the cell receptor-ECM ligand interaction (e.g., specific binding of a cell surface receptor to an ECM ligand on the surface of the biosensor) promotes a shift in the peak wavelength (PWV) of the intrinsic absorbance of the ECM-coated biosensor, the assay does not rely on washing off unbound cells, or on the addition any form of labeling to discriminate liganded (i.e., cells bound to the biosensor surface) from unliganded cells (i.e., cells not bound to the biosensor surface). Assays can be performed in microplate formats, for example microplates having about 96, 384, 1536, 3,456, 9,600 or more wells, providing the opportunity to perform large scale screening campaigns of small molecule or biologics that modify cell adhesion in ultra high throughput screening (uHTS) mode. A uHTS mode refers to screening more than about 50,000, 75,000, 100,000 compounds or more rapidly and can typically be in formats of 1536 well plates or other methodologies that allow economic testing of very large numbers of conditions or test reagents such as small organic molecules.

The ability to measure live cell signaling events promoted by a variety of extracellular stimuli acting through, for example, receptor tyrosine kinases, GPCRs, transient receptor potential channels, phopholipase C, signal transduction pathways (e.g. P13 kinases), cytokines, beta-arrestin pathway responses, cytoskeletal rearrangements, epigenetic signals (for example, changes in epigenetic modulators, e.g. histone deacetylases, can cause changes in signal transduction and downstream changes in ECM interaction of the cell, nuclear receptors, transcription factors, metabolic enzymes) and ion channel response can be dependent on the presence of an ECM interface coupling between cells and biosensor (i.e., the immobilization of cells having cell surface receptors (e.g., integrins) to ECM ligands immobilized on the surface of the biosensor). That is, in the absence of the cells being specifically immobilized to the biosensor via specific binding to ECM ligands that are immobilized to the biosensor surface, these cell responses to stimuli would not be detected or would be only weakly detected. Compounds that can stimulate cells include, e.g., hormones, growth factors, differentiation factors, morphogens, cytokines, chemokines, insulin, EGF, ATP, UTP, carbanoylcholine, acetylcholine, epinephrine, muscarine, compounds that induce osmolarity changes, compounds that induce membrane depolarization, small molecule test compounds, viruses, antibodies, polypeptides, antigens, polyclonal antibodies, monoclonal antibodies, single chain antibodies (scFv), F(ab) fragments, F(ab')$_2$ fragments, Fv fragments, small organic molecules (small organic molecules can have a molecular weight of more than 100 and less than about 2,500 Daltons (D); in one embodiment, small molecules are less than 2000, or less than 1500 or less than 1000 or less than 500 D), cells, bacteria, and biological samples, e.g., blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, and prostatic fluid.

The ability of biosensors to detect the presence of cells bearing cell surface receptors, e.g., integrin receptors, etc., only when the cell surface receptors are specifically bound to ECM ligands allows cell assays to be carried out in a homogenous format. That is, cell addition to the assay surface is immediately followed by detection, for example by colorimetric resonant reflectance detection, of bound cells without the need to wash unliganded (i.e., unbound) cells.

The invention provides homogenous assays to measure cellular responses to extracellular stimuli in a reconstituted system that circumvented lengthy, wash-dependent traditional protocols. Currently, typical cell-based assays used in high throughput screening campaigns such as FLIPR (Fluorescent Imaging Plate Reader) require lengthy wash-dependent steps. For example, traditional assays included the following steps:

1) Overnight cell plating in complete medium;
2) Cell washing with starvation buffer;
3) Starvation for 2 to 4 h;
4) Cell stimulation with various ligands.

A homogeneous assay of the invention can comprise washing cells with a buffered saline solution substantially lacking calcium and magnesium (such as Hank's buffered saline solution). Buffered saline solution substantially lacking or lacking calcium and magnesium contains less than about 1, 0.5, 0.01. 0.001% or less calcium and magnesium. The buffered saline solution is removed from the cells, and an isotonic ethylenediaminetetraacetate chealating agent is added to the cells. The isotonic ethylenediaminetetraacetate chealating agent is neutralized with buffered saline solution lacking calcium and magnesium. The previous steps are optionally performed. The cells are washed with buffered saline solution, optionally lacking calcium and magnesium. The biosensor has one or more ECM ligands immobilized to the surface, wherein the ECM ligands are specific for one or more cell surface receptors of the cell. The cells are added to the biosensor surface and allowed to attach to the surface of the biosensor. Optionally, the cells can be added to the biosensor surface in the presence or absence of an adhesion modulator. Optionally, the biosensor surface can have one or more extracellular matrix ligands immobilized to it. Optionally, the cells are mixed with one or more extracellular ligands or be derived as a mixture before they are added to the biosensor surface. The cells can have cell surface receptors specific for the one or more ECM ligands.

The augmentation of the signal response when cells are adhered specifically through cell surface receptors, e.g., integrins, etc. (and not non-specific interactions) is a significant advantage compared to other label-free or label-dependent systems that measure cellular responses.

Methods of the invention can be used to reconstitute a complex biological response by adding back individual components as they may be needed or discovered for facilitating a particular cellular function. That is, purified ECM ligands are immobilized onto the biosensor and then cells bearing cell surface receptors, such as integrin receptors, are plated onto the biosensor. If a viable ECM ligand to cell surface receptor interaction is established, cellular responses to extracellular stimuli that impinge upon cell adhesion give either a positive or negative shift (likely reflecting further engagement (positive shift) or disengagement of cell surface receptor and associated focal adhesion sites). From this point on, contribution of any other ECM ligands or stimulus on a given cell response can easily be assessed by addition of the purified ECM ligand or stimulus undergoing testing.

The ability to uniquely monitor specific cell surface receptor/extracellular matrix interactions on biosensors, e.g., colorimetric resonant reflectance biosensors or grating based waveguide biosensors, allows for a number of unique biological processes to be studied. For example, integrins are directly tied to cellular migration and chemotaxis. Therefore, using specially designed microplates with imbedded microfluidics, one can create a system where a common well delivers a gradient of chemotactic material to surrounding wells. Cells, adhered through specific cell surface receptor/ECM ligand binding, added to the surrounding wells, can be monitored for activation of the cytokine and migration properties in response to the gradient entering the surrounding well. Cells that are drawn to the chemotactic agent will pile up around the entry point of the microfluidic channel, and will yield a positive PWV signal (monitored at that location in the well), whereas cells that repel away from the agent will give a reduced PWV signal. Such a system could be used for any cell type that is known to undergo chemotaxis, including suspension cells such as platelets, neutrophils, monocytes, and the like, in addition to adherent cells.

Another system that is applicable is for ion channels, including ligand gated ion channels. Integrins can regulate ion channels and form macromolecular complexes. Furthermore, ligand gated ion channels feed back and can control integrin activation and/or expression. Therefore the ability to uniquely monitor integrin interactions can relate to effects observed on ligand gated ion channels.

For example, cells can be immobilized to a biosensor surface through a specific ECM ligand (for which the cell contains the complementary integrin or other protein) and allowed to adopt a quiescent signal. Modifying ionic conditions of cell culture medium or addition of other ion channel stimulus results in changes in cell volume as a result of changing osmolarity or ion channel activity (both voltage- and ligand-gated). For example, hyper-osmolarity leads to an increased cell volume whereas hypo-osmolarity results in smaller cell volume. Opening and closing of ion channels leads to flow of ions across the cell membranes that also been reported to result in cell volume changes. This volumetric cell change can be measured by the biosensor when the cell is anchored via cell surface receptors onto an optimized ECM ligand.

Additionally, there is a link between integrins and GPCR (both endogenous and over-expressed) or receptor tyrosine kinase (RTK) signaling. In fact, the integrin family of receptors plays a key role in regulating mitogenetic signal transduction pathways linked to RTKs. GPCRs, through their signal transduction pathways, ultimately converge on the same pathways shared by RTKs. In fact, a genetic deficiency has been described where impaired GPCR signaling gives rise to defective adhesion of leukocytes (Blood (101) 4437-4445 (2003)). Therefore, the ability to monitor changes in specific interactions between integrins and extracellular matrix proteins can be used to monitor GPCR and RTK responses.

For example, during inflammation cytokines and chemokines participate in well organized multi-receptor systems that orchestrate the attraction of fast moving monocytes as well as other circulating cells from the blood stream, onto the wall of blood vessels (endothelial cells) surrounding the inflamed tissue. This process is first triggered by slowing down circulating cells through selectins-mediated low affinity cell adhesion and eventually attaching the cells to the endothelium surrounding an inflamed tissue via integrins. Chemokines, acting through many different types of GPCR promote inside-out signaling that leads to the opening of integrin receptors, which are normally present in its closed conformation (hence the non-sticky nature of most blood cells). Upon opening of their integrins, monocytes come in contact with some integrin ligands like vascular cell adhesion molecules (VCAM), whose expression is transiently up-regulated in the inflamed endothelium. Following attachment, monocytes disengage their integrin receptors from the VCAMs and pass though the blood vessel wall and attack microbial agents that trigger the inflammation process in the first place In another embodiment, growth factors bind extracellular matrix and regulate cell growth, differentiation, and activation. A significant part of the mechanism by which growth factors acting through GPCRs or RTKs promote cell shape changes during mitosis, or cell migration and invasion during metastasis, involve regulation of levels of engagement of integrins. Different types of ECM ligands are immobilized to biosensors and potential growth factors are added to the surfaces of the biosensors. Specific PWV shift differences can be observed between the different coatings. Alternatively, cells are added to a biosensor having immobilized ECM ligand on its surface. The cells specifically bind to the ECM ligands via cell surface receptors. The cells are treated with different growth factors and the response of the cells is detected by, e.g., detection of PWV shifts.

One embodiment of the invention provides a method of determining if a test compound affects specific binding of cells to extracellular matrix ligands. The method comprises adding a first population of cells to a first colorimetric resonant reflectance biosensor or grating based waveguide biosensor surface, such as a microtiter plate well. The biosensor surface comprises immobilized extracellular matrix ligands, wherein the first population of cells has cell surface receptors specific for the extracellular matrix ligands. The first cells are allowed to attach to the surface of the first biosensor and a peak wavelength value or signal for the first cells is determined.

A second population of cells is added to a second colorimetric resonant reflectance biosensor or grating based waveguide biosensor surface, such as a second microtiter plate well. The second biosensor surface comprises immobilized extracellular matrix ligands. The second population of cells have cell surface receptors specific for the extracellular matrix ligands. A test compound is added to the second biosensor surface and the second cells are allowed to attach to the second surface of the biosensor. A peak wavelength value or signal for the second cells is determined. The peak wavelength value or signal obtained for the first cells is compared to the peak wavelength value or signal for the second cells. If the peak wavelength value or signal for the second cells is substantially different from the peak wavelength value or signal for the first cells, then the test compound affects specific binding of cells to extracellular matrix ligands.

Another embodiment of the invention provides a method of identifying a compound that affects adhesion of cells. One or more extracellular matrix ligands are immobilized to a surface of a colorimetric resonant reflectance biosensor or a grating-based waveguide biosensor, wherein the cells have cell surface receptors specific for the one or more extracellular matrix ligands. Cells are added to the biosensor. Alternatively, cells are mixed with one or more extracellular matrix ligands or are derived as a mixture of cells and ECM, wherein the cells have cell surface receptors specific for the one or more extracellular matrix ligands. The cells are then added, with one or more extracellular matrix ligands, to a surface of a colorimetric resonant reflectance biosensor or a grating-based waveguide biosensor. The cells are treated with a test compound. A colorimetric resonant reflectance optical first PWV or signal is detected and compared to a second PWV or signal from control cells that were not treated with the test compound to determine if the test compound affects adhesion of the cells. The test compound can be a compound that modulates the activity of a G protein-coupled receptor, an ion channel, P13 kinase, transient receptor potential channels, or phospholipase C. Optionally, after treating the cells with a test compound, an agent known to affect adhesion of the cells can be added to the test cells and to the control cells. Modulate means that the activity of a protein or compound is changed, for example, inhibited or increased.

Another embodiment of the invention provides a method of identifying a modified ECM ligand that affects adhesion of cells. ECM ligands like fibronectin and collagen are large proteinaceous materials. The cell integrins bind to specific amino acid sequences of the ECM ligands without the need or strict requirement for the larger protein context. A modified ECM ligand could thus be a very short peptide (e.g., a polypeptide containing an RGD motif) alone or fused to another protein such as Fc region of an IgG. A modified ECM ligand could be a slightly modified amino acid sequence known to bind particular integrins or adhesion proteins on cells. The purpose of the modified sequence might be to make it more tractable for therapeutic application, reduce the strength of the cell binding but not alter the specificity, make the specificity better/tighter, adapt the cell to attachment of other materials such as orthopedic, stent, or other bodily implants, modify orthopedic, stent, or other bodily implants for the attachment of selective cell types.

Cells are applied to a surface of a colorimetric resonant reflectance optical biosensor or a grating-based waveguide biosensor, wherein modified ECM ligands are immobilized to the surface of the biosensor. An agent known to affect adhesion of the cells is added to the cells. A colorimetric resonant reflectance optical first PWV or signal is detected for the cells and compared to a second PWV or signal from control cells that were added to a surface of a colorimetric resonant reflectance optical biosensor or the grating-based waveguide biosensor, wherein non-modified ECM ligands were immobilized to the surface of the biosensor to determine if the test compound affects adhesion of the cells.

Another embodiment of the invention provides a method of determining if a transfected cell produces a recombinant protein. When cells are transfected with a nucleic acid that encodes a protein, the cells must be tested to determine if the cells do indeed express the protein. One or more types of extracellular matrix ligands or cognate proteins known to interact with a protein expressed on the surface of a cell can be immobilized to the surface of a colorimetric resonant reflectance biosensor or a grating-based waveguide biosensor. Cells that have been transfected with a nucleic acid molecule that encodes a recombinant protein and that have cell surface receptors specific for the one or more extracellular matrix ligands are added to the surface of the biosensor. Alternatively, the transfected cells can be mixed, or be derived as a mixture, with one or more types of extracellular matrix ligands and then added to the surface of the biosensor. A first PWV or signal is determined. A modulator that causes a differential response in the transfected cells that expresses the recombinant protein as compared to transfected cells that do not express the recombinant protein is added to the biosensor. For example, a cell transfected to over express a particular G-protein coupled receptor (GPCR) or receptor tyrosine kinase (RTK) can be tested for specific response to known ligands to the GPCR or RTK, respectively, using a biosensor. Additionally, either transfected cell system could be compared for response using the known ligand(s) with the non-transfected "parental" cell line. A second PWV or signal is determined for the cells. The first peak wavelength value or signal is compared to the second peak wavelength value or signal. If the second peak wavelength value or signal is substantially different from the first peak wavelength value or signal, then the transfected cells express the recombinant protein. Additional steps can be performed prior to the determination of the second PWV or signal. For example, a selection medium (e.g., a medium containing an antibiotic) and the second PWV or signal can be determined. In one embodiment of the invention a PWV is determined using a high resolution scanner (a scanner have a resolution of about 1 microns to about 300 microns.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Current techniques for studying cell-protein interactions and other cell interactions are time consuming and labor intensive because they can involve many steps including radioisotope or fluorescence labeling, washing, blocking, and detecting. See e.g. Table 2. Current techniques for studying cell-protein interactions and other cell interactions can also use extensive amounts of expensive reagents. The instant invention provides compositions and methods for determining cell interactions that are faster than conventional methods and that require the use of fewer reagents than conventional methods.

The instant methods and compositions provide a label-free, simple, high throughput assay to identify cell specificity for specific binding substances, including proteins, cell migration, cell chemotaxis, specific binding substance-cell interactions, cell-extracellular matrix interactions, and cell-cell interactions.

In one embodiment of the invention the methods and compositions can reduce the usage of reagents significantly in cell assays. Reagent usage can be reduced by at least 100 times in comparison with microtiter plate whole well assays. More importantly, the simple image cell assays of the invention can replace current time consuming and labor intensive cell migration assays and cell chemotaxis assays with greater accuracy and reproducibility.

Colorimetric resonant reflectance optical biosensor technology is very sensitive to optical property changes due to biomolecules and biological cells interacting with the biosensor surface. This feature offers a great advantage for these biosensors in biological applications, such as investigating the interaction between biomolecules, including between biomolecules and biomolecules bound on a cell surface such as a cell surface receptor or a cell surface marker. Since colorimetric resonant reflectance optical biosensor technology directly detects biointeraction, the fluorescence label, radioisotope label, or biological tag such as enzymes and biological motifs are not needed. Colorimetric resonant reflectance optical biosensor cell attachment assays provide novel methods to directly detect the interaction between a molecule and its counterpart on a cell surface. The principle of a colorimetric resonant reflectance optical biosensor cell attachment assay is that the affinity binding between an immobilized target molecule and its counterpart on a cell surface will lead a cell to interact with the biosensor surface wherein this interaction can be detected.

One embodiment of the invention provides a vessel comprising a colorimetric resonant reflectance optical biosensor, wherein the colorimetric resonant reflectance optical biosensor comprises an internal surface of the vessel. For example, the colorimetric resonant reflectance optical biosensor can comprise a bottom surface of the vessel. One or more specific binding substances, such as two or more specific binding substances, are immobilized at two or more distinct locations on the internal surface of the vessel that comprises a colorimetric resonant reflectance optical biosensor. There may be different quantities of one specific binding substance at two or more distinct locations. A vessel can comprise, for example, a microtiter well, test tube, petri dish or a microfluidic channel. One embodiment of the invention provides a microtiter plate comprising one or more microtiter wells, wherein a bottom surface of the one or more microtiter wells comprises a colorimetric resonant reflectance optical biosensor. One or more specific binding substances can be immobilized at two or more distinct locations on the bottom surface of each microtiter well.

The invention provides methods of detecting binding of one or more types of cells to one or more specific binding substances. In one embodiment of the invention one or more types of cells are applied to an internal surface of a vessel. Any type of cell can be used, including, for example, prokaryotic cells, eukaryotic cells, artificial cells, cell membranes or artificial cell membranes. The cells can grow as, for example, adherent cells in culture or as suspension cells in culture. The internal surface of the vessel comprises a colorimetric resonant reflectance optical biosensor, wherein two or more specific binding substances are immobilized at two or more distinct locations on the internal surface of the vessel that comprises a colorimetric resonant reflectance optical biosensor. The vessel is illuminated with light and one or more peak wavelength values (PWVs) for each distinct location is detected. A peak wavelength value (PWV) is a relative measure of the binding substance and/or cells that are bound to the biosensor. If the one or more cells have bound to a specific binding substance, then the PWV is shifted at the distinct location to which the one or more cells are bound. The PWV is shifted in comparison to, for example, a portion of the biosensor that has no specific binding substance bound, or to a portion of the biosensor that has only specific binding substances bound, or to a given baseline PWV.

The one or more specific binding substances can be arranged in, for example an array of distinct locations on the internal surface of the vessel that comprises a colorimetric resonant reflectance optical biosensor. The distinct locations can define a microarray spot of about 50-500 microns in diameter. The one or more specific binding substances can be randomly arranged on the internal surface of the vessel. The one or more specific binding substances can be immobilized on the internal surface of the vessel that comprises a colorimetric resonant reflectance optical biosensor by a method such as physical adsorption, chemical binding, electrochemical binding, electrostatic binding, hydrophobic binding and hydrophilic binding, for example.

Another embodiment of the invention provides a method of detecting binding of one or more cells to a specific binding substance. The method comprises immobilizing one or more specific binding substances, such as two or more specific binding substances, at two or more distinct locations on an internal surface of a vessel, wherein the internal surface of the vessel comprises a colorimetric resonant reflectance optical biosensor and illuminating the vessel with light. One or more peak wavelength values for each distinct location are determined. One or more cells are applied to the internal surface of the vessel. The vessel is illuminated with light and one or more peak wavelength values are detected for each distinct location. The peak wavelengths are compared. If the one or more cells have bound to a specific binding substance, then the PWV is shifted at the distinct location to which the specific binding substance is bound.

Figure 2:
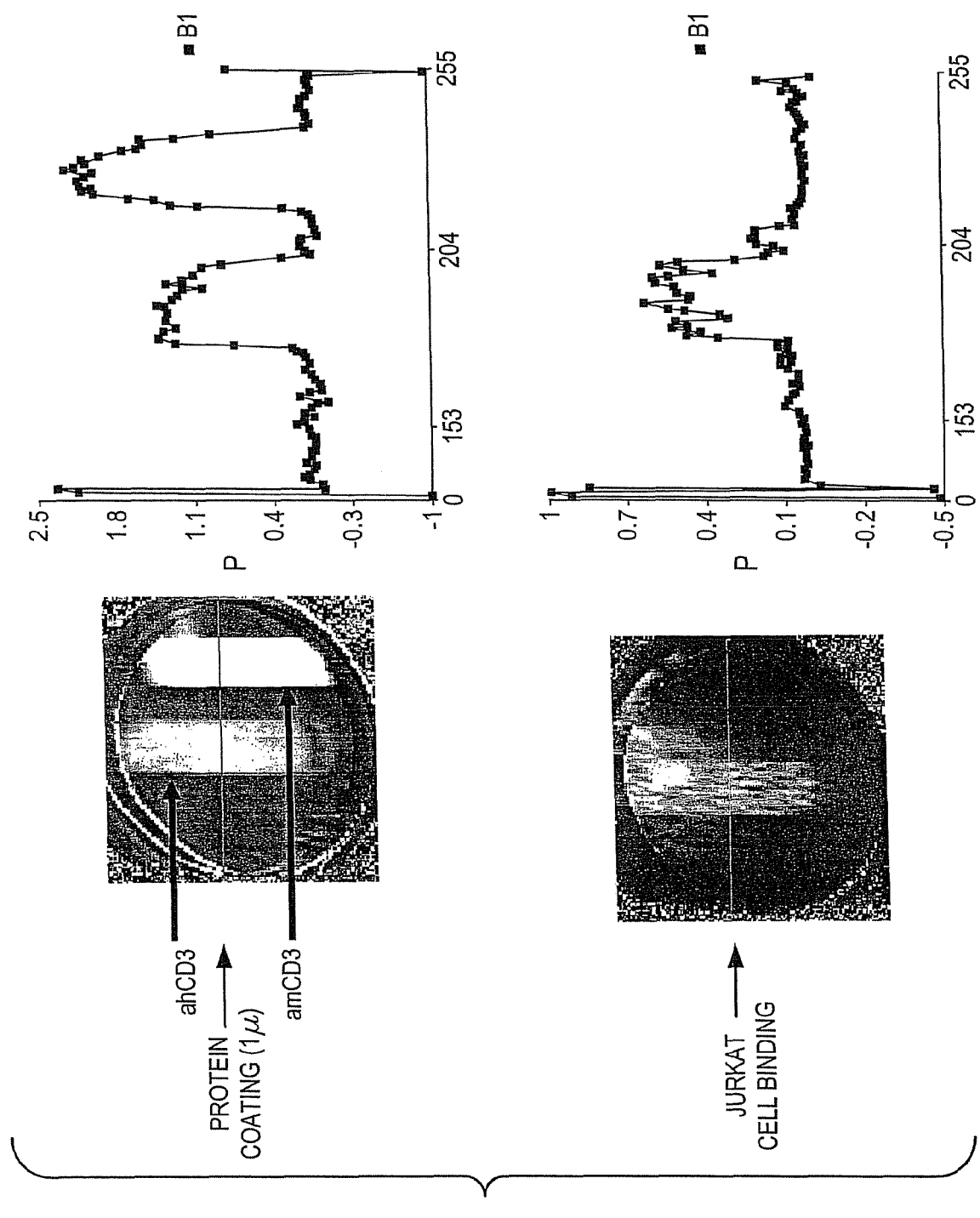
FIG. 2 shows the results from a cell-protein interaction assay.

In a working example, a microtiter well comprising a linear grating colorimetric resonant reflectance optical biosensor as an internal surface had 1 μl of anti-human CD3 and 1 μl of anti-mouse CD3 monoclonal antibody immobilized onto the surface of biosensor. See FIG. 1 and FIG. 2. The microtiter well was scanned and the antibody coating analyzed. See FIG. 2. After 20 min of incubation of Jurkat cells ($1 \times 10^5$) with the biosensor surface, the microtiter well was scanned and the cell attachment pattern was observed as shown in FIG. 2.

This assay clearly demonstrated that Jurkat cells interact with the distinct location that has been coated with ahCD3 inside of well from a 96 microplate biosensor and that no detectable signal from the distinct location with anti-mouse CD3 monoclonal antibody was observed.

These cell attachment assays can be used to identify molecules that are involved in cell adhesion, migration, chemotaxis, and invasion, for example. This assay can also be used to identify the cell surface molecules that regulate, for example, cell adhesion, migration, chemotaxis, and cell invasion. In addition, these assays can provide a novel tool to study cell-cell interactions, cell-matrix interactions, and cell-molecule interactions. Competition cell attachment assays can provide a novel tool for pharmaceutical drug screening to identify the compounds that specifically target molecules involved in cell interactions.

TABLE 2

| | | | | | Colorimetric Resonant Reflectance Biosensor | |
|---|---|---|---|---|---|---|
| | | Colorimetric | Fluorescence | Radioisotope | Adherent Cell | Suspension Cell |
| Plate Preparation | Coating Plate | 90 min | 90 min | 90 min | 30 min | 60 min |
| | Blocking | 30 min | 30 min | 30 min | — | — |
| | Harvest Cell | 30 min | 30 min | 30 min | 30 min | 30 min |
| Labeling Cell | Fluorescence Labeling | — | 45 min | | — | — |
| | 1 uCi 3[H] | — | — | 12-16 h | — | — |
| | Washing | — | 30 min | 30 min | — | — |

TABLE 2-continued

| | | Colorimetric | Fluorescence | Radioisotope | Colorimetric Resonant Reflectance Biosensor | |
|---|---|---|---|---|---|---|
| | | | | | Adherent Cell | Suspension Cell |
| Cell Adhesion | Incubation | 120 min | 120 min | 120 min | 120 min | 120 min |
| | Washing | 5 X PBS | 5 X PBS | 5 X PBS | — | — |
| Detection | | 10 min: fixing cell with 96% ethanol | — | — | — | — |
| | | 30 min: staining 0.1% crystal violet | — | — | — | — |
| | | 10 min: washing | — | — | — | — |
| | | 10 min: lysis cell 0.2% triton | 10 min: 10% FCS | 3% SDS lysis | — | — |
| | | Reading OD = 570 nm | Reading in fluorimetric plate reader | Scintillation | Directly real-time monitor cell interaction with sensor surface | Directly real-time monitor cell interaction with coated sensor |
| Total Assay Time (H) | | 5.5 h | 6 h | 16-20 h | 3 h | 3.5 h |

Example 2

Development of a Wash-Free CBA Protocol

Plating of CHO and HEK Cells Directly into Starvation Medium

The first established protocol for cell based assays using biosensor technology relies primarily on two important steps referred to as cell washing and starvation.

These steps are important in reducing assay time as cell harvesting is currently carried out by trypsin treatment of large scale cultures. Cell harvesting is currently carried out by trypsin treatment of large scale cultures. Trypsinization of cell monolayers is effective and reproducible and can be easily adapted to most cell lines. In practicality, trypsin mediated cell harvesting is a two step process whereby supplemented tissue culture media is washed off tissue culture flaks in a divalent cation-free buffer (Hank's buffered saline solution, HBSS) followed by trypsinization of cellular junctions in the presence of EDTA. The absence of Ca++ weakens and/or breaks down protein-protein interaction events that mediate cell-cell (adherens, gap and tight junctions, depending on the cell type) contacts and cell-substrate (extracellular, ECM) interactions, mediated by integrin and other EMC receptors. Proteolysis of these trans-membrane components, along with all other transmembrane receptors yields a homogenous cell suspension unable to respond to extracellular stimuli.

Overnight cell plating in appropriate cell culture medium for each cell line supplemented with a required serum complement from different animal sources (bovine, horse and either calf or fetal, etc.) ensures that cells are grown in a osmolarity-balanced, pH-controlled amino acids-, vitamins-, sugars- and growth factors-rich medium. This allows full recovery of cells plated on biosensor plates, following harvesting by trypsin treatment.

Although cells have reestablished a full complement of trans-membrane proteins and have restored cell-cell and cell-substrate interactions, the presence of growth factor-rich medium can mask cell stimulation promoted by growth factor receptors (RTKs and GPCRs) or cellular responses to hormones, cytokines, growth factors and any extracellular stimuli that signals through pathways such as the PI-3 kinase/Akt pathways, small G-proteins of the Ras super family/MAP/Erk/JNK kinases pathways, etc. On the other hand the presence of amino acids triggers activation of the mTor/Akt/S6-kinase pathway, blunting signaling through these AGC kinases.

As mentioned, supplemented medium removal is therefore a critical step that widens feasibility studies to establish whether a given target or pathway will be tractable through biosensor technology.

Several issues arise with the need to wash microtiter biosensor plates before compound and/or ligand testing. Lack of an accurate cell washer or automated liquid handling (ALH) results in variable volumes in each well of the plate, which in turn results in variable dilution of compounds being tested making it impossible to run accurate direct well to well comparisons. However, precise plate washing using ALH systems results in a lengthy protocol that can take from 12 to 25 minutes per plate. To overcome the bottleneck steps of cell-washing and starvation, we have investigated alternative protocols that: a) bypass cell harvesting using trypsin; and b) still rely on trypsin harvesting, but allow normally adherent cells to recover while cells are maintained in suspension. These options have allowed us to plate cells in nutrient reduced or depleted medium and growth factor reduced or depleted medium. That is, the cells can be directly plated in starvation buffer.

Versene harvested CHO and HEK cells were plated in starvation medium with or without serum coating as follows. About 80% confluent cell monolayers were gently washed with HBSS lacking Ca++ and Mg++. After letting cells sit in HBSS for 2 to 3 minutes, buffer was aspirated and cells were treated with an isotonic Versene solution (Gibco) for about 10 minutes at 37° C. Cells were released from flasks by tapping for an additional 2 minutes. Versene was neutralized by diluting it in 10 volumes of HBSS containing 10 mM Hepes, 5 mM glucose, 2 mM Ca++ and Mg++ and 1% penicillin/streptomycin antibiotics (SM) and cells were spun down and washed once with SM with and then plated on 384 sensors containing 25 μl of SM. Cells were spun down and allowed to attach for varying periods of time.

Positive stimuli controls included (1) insulin and ATP or (2) UTP, which stimulate endogenously expressed receptors of the RTK and GPCR type, respectively. These stimuli produce robust PWV shifts that range from 100 to 300 pm in overnight plated cells in full medium after wash and starvation) of Versene harvested cells plated in supplemented HBSS on biosensor plates without poly-D-lysine (PDL) or serum precoating were all indistinguishable from control wells (no stimuli) with shifts <20 pM. Stimuli responses of Versene harvested cells plated in supplemented HBSS on sensor plates with PDL and without serum precoating were indistinguishable from control wells (no stimuli) with shifts <20 pM. Cell responses to stimuli of Versene harvested cells plated in supplemented HBSS on $TiO_2$ biosensor plates sensor coated with increasing serum concentration (without PDL precoat) resulted in PVW shift responses virtually indistinguishable, in terms of kinetics, magnitude of shift and EC50 values from overnight plated cells in complete medium.

Trypsin harvested CHO and HEK cells were plated in starvation medium with varying serum coating concentrations. About 80% confluent cell monolayers were gently washed with HBSS and then trypsinized for 2 to 5 minutes. Trypsinization was stopped with complete medium and cells were spun down and resuspended in complete medium and then allowed to "recover" at room temperature (incubation at 37° C. can also be done) in complete medium (about 100 K cells/ml) in a 50 ml Falcon tube.

After 7 hours cells were spun down and washed twice with HBSS containing 10 mM Hepes, 5 mM glucose, 2 mM Ca++ and Mg++ and 1% Pen/Strep (SM) and then plated on 384 sensors containing 25 μl of SM. Cells were spun down and allowed to attach overnight.

Cells plated in this manner looked indistinguishable from cells plated in complete medium and gave robust responses. Kinetic of PWV shift response, magnitude or amplitude of PWV shift and EC50 dose for the stimuli tested) to ATP (25 uM), UTP (100 uM), EGF (50 nM), Insulin (1.5 uM), Prostaglandin (100 pM) and Muscarin (10 uM). Responses ranged from about 60% to 120% of those seen in common overnight plating conditions reported in the scientific literature.

In addition to bypassing the step of cell washing and improving workflow, wash-free protocols will more importantly enable the use of biosensors in HTS formats that use 1536 or more well plates. Adding an ECM ligand(s) coating in half of the working volume followed by addition of cells in the other half, followed by compound addition simplifies the use of 1536 well plates to a wash-free, three addition steps protocol.

Other approaches could provide alternatives for those cells that fail to attach and give signal with the protocols described herein. Cell plating in low serum (0.25%), in other wise complete medium, may help sensitive cells or freshly thawed out cells (plating and assaying straight out liquid $N_2$ stocks). Dilution of complete medium may prove sufficient to starve cells and lower phospho-signaling pathways. Methods of this invention make unnecessary the inclusion of significant amounts of serum in the starvation buffer medium to enhance performance of sensitive primary cells.

Coating colorimetric resonant reflectance biosensors with various concentrations of fibronectin and collagen has confirmed that direct cell plating in starvation buffer is feasible for the following cell types: CHO-K1, HEK-293, THP-1 (endogens receptors) and recombinant cells mP-M4, mP-M5, mP-ET and CHO-M3, among others.

Depending on the cell type and the surface coating, cell responses using the "no-wash", short plating protocol provide PWV shifts between about 10-300 pm, or about 100-200 pm shift, or about >150 pm.

Example 3

Collagen Coating and Storage of Colorimetric Resonant Reflectance Biosensors: Performance Evaluation Using mP-M4 Cells Conditions were evaluated for coating a colorimetric resonant reflectance biosensor with the extracellular matrix (ECM) protein collagen (COLL) and storage of the resulting coated biosensor. Collagen I has been identified as a culturing substrate that mediates the attachment of muscle cells, hepatocytes, spinal ganglion, embryonic lung cells, Schwann cells, among other primary cells. Collagen is a specific ECM ligand for 14 Chem-1 cells. These cells over express muscarinic GPCRs M4 and respond to carbachol in a dose dependent manner when plated on freshly deposited collagen coated colorimetric resonant reflectance biosensor.

Three different colorimetric resonant reflectance 384-well biosensor plates were coated with different concentrations of collagen in couplet rows. The plates were stored dry or stored in glycerol or freshly made. The freshly made collagen plates will be compared to plates that have been made and dried and plates that were made and stored in a 60% glycerol solution.

Bare colorimetric resonant reflectance $TiO_2$ 384 well biosensor plates were plasma treated for 2 minutes. ECM proteins were purchased from Sigma-Aldrich. The collagen was from calf skin solution, sterile-filtered, 1 mg/ml protein in 0.1 M acetic acid, cell culture tested. The fibronectin was from human plasma cell culture tested.

The plates were hydrated with 1×PBS for 15 min and washed with 1×PBS using a Biotek plate washer. An ECM coating solution (25 ml/well) was added to the wells. ECM, PDL and FBS coating solutions are prepared sterile in 1×PBS. Collagen was used at several concentrations (0.62, 1.25, 2.5, 5.0, 10.0, 20.0 ug/ml) and PDL at 2 mg/ml and FBS at 2%. Collagen was coated onto the plates for 2 h at 37° C. and then washed with 1×PBS using a plate washer. The biosensor was blocked with 0.2% BSA in PBS for 30 min at room temperature and then washed with 1×HBBS using a plate washer. 25 ml of Starvation Buffer (HBSS supplemented with 2 mM Ca++ and Mg++, 5 mM Glucose [10 mM final], 10 mM Hepes, Penicillin and streptomycin 1% v/v and 0.01% BSA was added to the plates and PWV were determined for the wells. This is the starvation buffer baseline.

Cell monolayers were grown overnight in tissue culture (TC) flasks and washed. The cells were detached by trypsin treatment at 37° C. for about 5 to 6 minutes. Attachment of mP-M4 and mP-M5 was particularly firm to polystyrene TC flask. The trypsin was neutralized with complete medium and the cells were spun down. The cells were resuspended in complete medium (about 25 ml per flask at 80 to 90% confluency) and incubated for 3 to 4 hours in TC incubator. The cells were spun down and resuspended in starvation buffer. The cells were then read for plating.

Cell suspension (25 ml) of in starvation buffer (about 40,000 cells) were added to wells of 384 biosensor plate. The cell plate was spun on a centrifuge (2 min) to aid cell attachment. Cells were allowed to re-attach to the biosensor plate during a three hour incubation at 37° C. PWVs were determined for the wells. This is the cell attachment reading. 25 μl of carbachol solution (a cell stimulus) was added to the wells of the biosensor plates. Treatment of cells expressing M1-M5 Muscarinic receptors with carbachol results in a positive PWV shift ranging from 500 to 2000 pm. The cells bind to carbachol via GPCR receptors and the biosensor can detect the cell response to the GPCR binding event via a shift in PWV.

Two plates were coated 2 days before the cell assay, one for dry storage and one for glycerol storage. The 3rd plate was made "fresh" the day of the cell assay. A single deep well compound plate was made containing a serial dilution (⅓) of carbachol starting at 10 mM and covering 11 concentrations+ buffer control with each concentration loaded as duplicate sets of columns.

Biosensor coating with collagen provides a surface that results in superior performance of mP-M4 cells with lower EC50 concentrations compared to PDL and FBS coated surfaces. Cell shifts are significantly higher on the dried down collagen as compared to fresh and glycerol stored collagen plates, but gives poorer EC50 response. Glycerol stored collagen coated plates have similar results to fresh made collagen plates. These experiments demonstrate that with Mp-M4 cells, an EC50 concentration 10 times lower was observed for a freshly made PDL surface than for one that has been dried down. Glycerol stored plates at −20 C demonstrate performance that is the same as freshly made plates

We claim:

1. A method of detection of responses of cells to stimuli comprising:
   (a) (i) immobilizing one or more extracellular matrix ligands to a surface of a colorimetric resonant reflectance biosensor or a grating-based waveguide biosensor, wherein the cells have cell surface receptors specific for the one or more extracellular matrix ligands; and adding the cells to the biosensor; or
   (ii) mixing cells with one or more extracellular matrix ligands, wherein the cells have cell surface receptors specific for the one or more extracellular matrix ligands; and adding the cells with one or more extracellular matrix ligands to a surface of a colorimetric resonant reflectance biosensor or a grating-based waveguide biosensor;
   (b) exposing the cells to stimuli, wherein the stimuli are compounds that modulate activity of a G protein-coupled receptor, ion channels, P13 kinase, transient receptor potential channels, phospholipase C, receptor tyrosine kinases, cytokines, beta-arrestin pathway responses, cytoskeletal rearrangements, epigenetic signals, integrins, or signal transduction pathways; and
   (c) detecting a change in peak wavelength value or signal over time, which indicates that the cells have responded to the stimuli.

2. The method of claim 1, wherein the cells of (a) are in serum-free medium.

3. The method of claim 2, wherein the exposing of the cells to stimuli is done without washing off the serum-free medium.

4. The method of claim 1, wherein prior to (a) the cells are washed with buffered saline.

5. The method of claim 4, wherein the buffered saline substantially lacks calcium and magnesium.

6. The method of claim 1, wherein prior to step (a), the following steps are performed:
   (i) washing the cells with a buffered saline solution lacking calcium and magnesium;
   (ii) removing the buffered saline solution lacking calcium and magnesium from the cells;
   (iii) adding an isotonic ethylenediaminetetraacetate chealating agent to the cells;
   (iv) neutralizing the isotonic ethylenediaminetetraacetate chealating agent with buffered saline solution.

7. The method of claim 1, wherein the cells are added to the biosensor surface in the presence of an adhesion modulator.

8. The method of claim 1, wherein the detecting the response of the cells to the stimuli is done with a detection device with a resolution of about 2 to 10 micrometers.

9. The method of claim 1, wherein the response of the cells to stimuli are changes in cell growth patterns, changes in cell death patterns, changes in cell movement, changes in cell size or volume, or changes in cell adhesion.

* * * * *